United States Patent
Forsell

(10) Patent No.: US 8,290,594 B2
(45) Date of Patent: Oct. 16, 2012

(54) IMPOTENCE TREATMENT APPARATUS WITH ENERGY TRANSFORMING MEANS

(75) Inventor: Peter Forsell, Bouveret (CH)

(73) Assignee: Obtech Medical AG, Baar (CH)

( * ) Notice: Subject to any disclaimer, the term of this patent is extended or adjusted under 35 U.S.C. 154(b) by 0 days.

(21) Appl. No.: 12/859,454

(22) Filed: Aug. 19, 2010

(65) Prior Publication Data

US 2011/0040143 A1   Feb. 17, 2011

Related U.S. Application Data

(63) Continuation of application No. 10/203,085, filed as application No. PCT/SE01/00268 on Feb. 9, 2001, now abandoned.

(60) Provisional application No. 60/182,103, filed on Feb. 11, 2000, provisional application No. 60/182,104, filed on Feb. 11, 2000.

(51) Int. Cl.
*A61F 2/26* (2006.01)

(52) U.S. Cl. .......................... 607/39; 600/40

(58) Field of Classification Search .......... 607/2, 39–41, 607/143; 600/29–31, 38–41; 623/14.13
See application file for complete search history.

(56) References Cited

U.S. PATENT DOCUMENTS

| | | | |
|---|---|---|---|
| 2,060,913 A | 11/1936 | Weaver | |
| 2,795,641 A | 6/1957 | Ross | |
| 3,209,081 A | 9/1965 | Ducote et al. | |
| 3,598,287 A | 8/1971 | De Man | |
| 3,662,758 A * | 5/1972 | Glover | 607/40 |
| 3,692,027 A | 9/1972 | Ellinwood, Jr. | |
| 3,731,679 A | 5/1973 | Wilhelmson et al. | |
| 3,731,681 A | 5/1973 | Blackshear et al. | |
| 3,750,194 A | 8/1973 | Summers | |
| 3,817,237 A | 6/1974 | Bolduc | |
| 3,855,122 A | 12/1974 | Bourganel | |
| 3,863,622 A | 2/1975 | Buuck | |
| 3,875,928 A | 4/1975 | Angelchik | |
| 3,923,060 A | 12/1975 | Ellinwood, Jr. | |
| 3,954,102 A | 5/1976 | Buuck | |
| 4,003,379 A | 1/1977 | Ellinwood, Jr. | |
| 4,009,711 A | 3/1977 | Uson | |

(Continued)

FOREIGN PATENT DOCUMENTS

DE   19511998   10/1996

(Continued)

OTHER PUBLICATIONS

Publication No. EP 1568338A2, dated Aug. 31, 2005, for European Patent Application No. 05010107.0.

(Continued)

*Primary Examiner* — Scott Getzow
*Assistant Examiner* — Joseph Stoklosa
(74) *Attorney, Agent, or Firm* — Nixon & Vanderhye P.C.

(57) ABSTRACT

A male sexual impotence treatment apparatus includes or use an operable restriction device implantable in a male patient for engaging a tissue portion of the penile tissue to form a restrictable passageway for the penile exit blood flow. An energy transmission device is provided for wireless transmission of energy from outside the patient's body to inside the patient's body for use in connection with the operation of the restriction device, including temporarily contracting said tissue portion to restrict the penile exit blood flow in the blood flow passageway to achieve erection.

142 Claims, 7 Drawing Sheets

U.S. PATENT DOCUMENTS

| | | | |
|---|---|---|---|
| 4,026,305 A | 5/1977 | Brownlee et al. |
| 4,044,401 A | 8/1977 | Guiset |
| 4,201,202 A | 5/1980 | Finney et al. |
| 4,221,219 A | 9/1980 | Tucker |
| 4,235,222 A | 11/1980 | Ionescu |
| 4,243,306 A | 1/1981 | Bonini |
| 4,246,893 A | 1/1981 | Berson |
| 4,265,241 A | 5/1981 | Portner et al. |
| 4,271,827 A | 6/1981 | Angelchik |
| 4,274,407 A | 6/1981 | Scarlett |
| 4,304,225 A | 12/1981 | Freeman |
| 4,318,396 A | 3/1982 | Finney |
| 4,342,308 A | 8/1982 | Trick |
| 4,369,771 A | 1/1983 | Trick |
| 4,400,169 A | 8/1983 | Stephen |
| 4,412,530 A | 11/1983 | Burton |
| 4,424,807 A | 1/1984 | Evans |
| 4,505,710 A | 3/1985 | Collins |
| 4,509,947 A | 4/1985 | Lattin |
| 4,542,753 A | 9/1985 | Brenman et al. |
| 4,550,720 A | 11/1985 | Trick |
| 4,556,050 A | 12/1985 | Hodgson et al. |
| 4,559,930 A | 12/1985 | Cobiski |
| 4,563,175 A | 1/1986 | LaFond |
| 4,583,523 A | 4/1986 | Kleinke et al. |
| 4,584,994 A | 4/1986 | Bamberger et al. |
| 4,592,339 A | 6/1986 | Kuzmak et al. |
| 4,592,355 A | 6/1986 | Antebi |
| 4,599,081 A | 7/1986 | Cohen |
| 4,602,621 A | 7/1986 | Hakky |
| 4,610,658 A | 9/1986 | Buchwald et al. |
| 4,623,350 A | 11/1986 | Lapeyre et al. |
| 4,628,928 A | 12/1986 | Lowell |
| 4,664,100 A | 5/1987 | Rudloff |
| 4,677,534 A | 6/1987 | Okochi |
| 4,679,560 A | 7/1987 | Galbraith |
| 4,696,288 A | 9/1987 | Kuzmak et al. |
| 4,711,231 A | 12/1987 | Finegold et al. |
| 4,723,538 A | 2/1988 | Stewart et al. |
| 4,756,949 A | 7/1988 | Spence et al. |
| 4,771,780 A | 9/1988 | Sholder |
| 4,828,544 A | 5/1989 | Lane et al. |
| 4,828,990 A | 5/1989 | Higashi et al. |
| 4,829,990 A | 5/1989 | Thuroff et al. |
| 4,846,794 A | 7/1989 | Hertzer |
| 4,902,279 A | 2/1990 | Schmidtz et al. |
| 4,925,443 A | 5/1990 | Heilman et al. |
| 4,941,461 A | 7/1990 | Fischell |
| 4,942,668 A | 7/1990 | Franklin |
| 4,958,630 A | 9/1990 | Rosenbluth et al. |
| 4,979,955 A | 12/1990 | Smith |
| 4,982,731 A | 1/1991 | Lue et al. |
| 4,983,177 A | 1/1991 | Wolf |
| 5,006,106 A | 4/1991 | Angelchik |
| 5,012,822 A | 5/1991 | Schwarz |
| 5,042,084 A | 8/1991 | Daly |
| 5,048,511 A | 9/1991 | Rosenbluth et al. |
| 5,057,075 A | 10/1991 | Moncrief et al. |
| 5,062,416 A | 11/1991 | Stucks |
| 5,074,868 A | 12/1991 | Kuzmak |
| 5,098,369 A | 3/1992 | Heilman et al. |
| 5,112,202 A | 5/1992 | Oshima et al. |
| 5,123,428 A | 6/1992 | Schwarz |
| 5,160,338 A | 11/1992 | Vincent |
| 5,226,429 A | 7/1993 | Kuzmak |
| 5,250,020 A | 10/1993 | Bley |
| 5,297,536 A | 3/1994 | Wilk |
| 5,304,206 A | 4/1994 | Baker, Jr. et al. |
| 5,316,543 A | 5/1994 | Eberbach |
| 5,358,474 A | 10/1994 | Kaldany |
| 5,415,660 A | 5/1995 | Campbell et al. |
| 5,437,605 A | 8/1995 | Helmy |
| 5,449,368 A | 9/1995 | Kuzmak |
| 5,453,079 A | 9/1995 | Schwaninger |
| 5,454,840 A | 10/1995 | Krakovsky et al. |
| 5,501,703 A | 3/1996 | Holsheimer et al. |
| 5,505,733 A | 4/1996 | Justin et al. |
| 5,509,888 A | 4/1996 | Miller |
| 5,518,504 A | 5/1996 | Polyak |
| 5,540,731 A | 7/1996 | Testerman |
| 5,569,187 A | 10/1996 | Kaiser |
| 5,578,069 A | 11/1996 | Miner, II |
| 5,582,580 A | 12/1996 | Buckman, Jr. et al. |
| 5,665,065 A | 9/1997 | Colman et al. |
| 5,676,674 A | 10/1997 | Bolanos et al. |
| 5,690,108 A | 11/1997 | Chakeres |
| 5,702,431 A | 12/1997 | Wang et al. |
| 5,704,893 A | 1/1998 | Timm |
| 5,735,887 A | 4/1998 | Barreras et al. |
| 5,749,909 A | 5/1998 | Schroeppel et al. |
| 5,769,877 A | 6/1998 | Barreras |
| 5,771,903 A | 6/1998 | Jakobsson |
| 5,814,020 A | 9/1998 | Gross |
| 5,823,991 A | 10/1998 | Shim |
| 5,827,286 A | 10/1998 | Incavo et al. |
| 5,848,962 A | 12/1998 | Feindt et al. |
| 5,858,001 A | 1/1999 | Tsals et al. |
| 5,876,425 A | 3/1999 | Gord et al. |
| 5,900,909 A | 5/1999 | Parulski et al. |
| 5,902,336 A | 5/1999 | Mishkin |
| 5,910,149 A | 6/1999 | Kuzmak |
| 5,928,195 A | 7/1999 | Malamud et al. |
| 5,938,584 A | 8/1999 | Ardito et al. |
| 5,938,669 A | 8/1999 | Klaiber et al. |
| 5,954,715 A | 9/1999 | Harrington et al. |
| 5,964,789 A | 10/1999 | Karsdon |
| 5,978,712 A | 11/1999 | Suda et al. |
| 5,995,874 A | 11/1999 | Borza |
| 5,997,501 A | 12/1999 | Gross et al. |
| 6,003,736 A | 12/1999 | Ljunggren |
| 6,067,991 A | 5/2000 | Forsell |
| 6,074,341 A | 6/2000 | Anderson et al. |
| 6,077,215 A | 6/2000 | Leysieffer |
| 6,095,968 A | 8/2000 | Snyders |
| 6,102,887 A | 8/2000 | Altman |
| 6,102,922 A | 8/2000 | Jakobsson et al. |
| 6,113,574 A | 9/2000 | Spinello |
| 6,116,193 A | 9/2000 | Goeckner |
| 6,117,067 A | 9/2000 | Gil-Vernet |
| 6,134,470 A | 10/2000 | Hartlaub |
| 6,135,945 A | 10/2000 | Sultan |
| 6,145,505 A | 11/2000 | Nikolchev et al. |
| 6,162,238 A | 12/2000 | Kaplan et al. |
| 6,185,452 B1 | 2/2001 | Schulman et al. |
| 6,197,055 B1 | 3/2001 | Matthews |
| 6,210,347 B1 | 4/2001 | Forsell |
| 6,221,060 B1 | 4/2001 | Willard |
| 6,233,474 B1 | 5/2001 | Lemelson |
| 6,275,737 B1 | 8/2001 | Mann |
| 6,319,191 B1 | 11/2001 | Sayet et al. |
| 6,332,466 B1 | 12/2001 | Yoon |
| 6,346,099 B1 | 2/2002 | Altman |
| 6,436,054 B1 | 8/2002 | Viola et al. |
| 6,450,173 B1 | 9/2002 | Forsell |
| 6,450,946 B1 | 9/2002 | Forsell |
| 6,453,907 B1 | 9/2002 | Forsell |
| 6,454,698 B1 | 9/2002 | Forsell |
| 6,454,699 B1 | 9/2002 | Forsell |
| 6,454,700 B1 | 9/2002 | Forsell |
| 6,454,701 B1 | 9/2002 | Forsell |
| 6,456,883 B1 | 9/2002 | Torgerson et al. |
| 6,460,543 B1 | 10/2002 | Forsell |
| 6,461,292 B1 | 10/2002 | Forsell |
| 6,461,293 B1 | 10/2002 | Forsell |
| 6,463,935 B1 | 10/2002 | Forsell |
| 6,464,628 B1 | 10/2002 | Forsell |
| 6,470,892 B1 | 10/2002 | Forsell |
| 6,471,635 B1 | 10/2002 | Forsell |
| 6,475,136 B1 | 11/2002 | Forsell |
| 6,482,145 B1 | 11/2002 | Forsell |
| 6,503,189 B1 | 1/2003 | Forsell |
| 6,571,127 B1 | 5/2003 | Ben-Haim et al. |
| 6,572,585 B2 | 6/2003 | Choi |
| 6,589,229 B1 | 7/2003 | Connelly et al. |
| 6,638,208 B1 | 10/2003 | Natarajan et al. |
| 6,638,303 B1 | 10/2003 | Campbell |
| 6,659,936 B1 | 12/2003 | Furness et al. |

| | | |
|---|---|---|
| 6,678,561 B2 | 1/2004 | Forsell |
| 6,689,085 B1 | 2/2004 | Rubenstein et al. |
| 6,709,385 B2 | 3/2004 | Forsell |
| 6,740,075 B2 | 5/2004 | Lebel et al. |
| 6,772,011 B2 | 8/2004 | Dolgin |
| 6,895,280 B2 | 5/2005 | Meadows et al. |
| 6,911,002 B2 | 6/2005 | Fierro |
| 6,915,165 B2 | 7/2005 | Forsell |
| 6,948,918 B2 | 9/2005 | Hansen |
| 6,953,429 B2 | 10/2005 | Forsell |
| 6,960,233 B1 | 11/2005 | Berg et al. |
| 6,979,351 B2 | 12/2005 | Forsell et al. |
| 7,011,624 B2 | 3/2006 | Forsell |
| 7,017,583 B2 | 3/2006 | Forsell |
| 7,043,295 B2 | 5/2006 | Starkebaum |
| 7,066,922 B2 | 6/2006 | Angel et al. |
| 7,108,686 B2 | 9/2006 | Burke et al. |
| 7,207,936 B2 | 4/2007 | Forsell |
| 7,235,044 B2 | 6/2007 | Forsell |
| 7,238,165 B2 | 7/2007 | Vincent |
| 7,250,037 B2 | 7/2007 | Shermer et al. |
| 7,311,690 B2 | 12/2007 | Burnett |
| 7,338,437 B2 | 3/2008 | Forsell |
| 7,367,938 B2 | 5/2008 | Forsell |
| 7,371,208 B2 | 5/2008 | Forsell |
| 7,395,822 B1 | 7/2008 | Burton et al. |
| 7,407,479 B2 | 8/2008 | Forsell |
| 7,407,481 B2 | 8/2008 | Forsell |
| 7,442,165 B2 | 10/2008 | Forsell |
| 7,455,663 B2 | 11/2008 | Bikovsky |
| 7,569,050 B2 | 8/2009 | Moberg et al. |
| 7,621,863 B2 | 11/2009 | Forsell |
| 7,648,455 B2 | 1/2010 | Forsell |
| 7,666,132 B2 | 2/2010 | Forsell |
| 7,669,601 B2 | 3/2010 | Tal |
| 7,846,160 B2 | 12/2010 | Payne et al. |
| 7,972,354 B2 | 7/2011 | Prestezog et al. |
| 7,987,853 B2 | 8/2011 | Swann et al. |
| 2001/0011543 A1 | 8/2001 | Forsell |
| 2001/0016738 A1 | 8/2001 | Harrington et al. |
| 2002/0022759 A1 | 2/2002 | Forsell |
| 2002/0028980 A1 | 3/2002 | Thierfelder et al. |
| 2002/0040208 A1 | 4/2002 | Flaherty et al. |
| 2002/0055711 A1 | 5/2002 | Lavi et al. |
| 2002/0072698 A1 | 6/2002 | Chiang et al. |
| 2002/0072759 A1 | 6/2002 | Fry |
| 2002/0095139 A1 | 7/2002 | Keogh et al. |
| 2002/0095164 A1 | 7/2002 | Andreas |
| 2002/0151922 A1 | 10/2002 | Hogendijk et al. |
| 2002/0165575 A1 | 11/2002 | Saleh |
| 2002/0183588 A1 | 12/2002 | Fierro |
| 2003/0009221 A1 | 1/2003 | Forsell |
| 2003/0014010 A1 | 1/2003 | Carpenter et al. |
| 2003/0014086 A1 | 1/2003 | Sharma |
| 2003/0021822 A1 | 1/2003 | Lloyd |
| 2003/0032855 A1 | 2/2003 | Shahinpoor |
| 2003/0032857 A1 | 2/2003 | Forsell |
| 2003/0050591 A1 | 3/2003 | Patrick McHale |
| 2003/0055442 A1 | 3/2003 | Laufer et al. |
| 2003/0060893 A1 | 3/2003 | Forsell |
| 2003/0066536 A1 | 4/2003 | Forsell |
| 2003/0069547 A1 | 4/2003 | Gonon |
| 2003/0088148 A1 | 5/2003 | Forsell |
| 2003/0092962 A1 | 5/2003 | Forsell |
| 2003/0100929 A1 | 5/2003 | Forsell |
| 2003/0105385 A1 | 6/2003 | Forsell |
| 2003/0109771 A1 | 6/2003 | Forsell |
| 2003/0125605 A1 | 7/2003 | Forsell |
| 2003/0125768 A1 | 7/2003 | Peter |
| 2003/0144648 A1 | 7/2003 | Forsell |
| 2003/0163029 A1 | 8/2003 | Sonnenschein et al. |
| 2003/0208247 A1 | 11/2003 | Spinelli et al. |
| 2003/0233143 A1 | 12/2003 | Gharib et al. |
| 2004/0024285 A1 | 2/2004 | Muckter |
| 2004/0024419 A1 | 2/2004 | Slepian et al. |
| 2004/0034275 A1 | 2/2004 | Forsell |
| 2004/0068299 A1 | 4/2004 | Laske et al. |
| 2004/0089313 A1 | 5/2004 | Utley et al. |
| 2004/0098113 A1 | 5/2004 | Forsell et al. |
| 2004/0102804 A1 | 5/2004 | Chin |
| 2004/0122526 A1 | 6/2004 | Imran |
| 2004/0122527 A1 | 6/2004 | Imran |
| 2004/0147871 A1 | 7/2004 | Burnett |
| 2004/0162568 A1 | 8/2004 | Saadat et al. |
| 2004/0177918 A1 | 9/2004 | Murata et al. |
| 2004/0249451 A1 | 12/2004 | Lu et al. |
| 2004/0260316 A1 | 12/2004 | Knudson et al. |
| 2005/0038484 A1 | 2/2005 | Knudson et al. |
| 2005/0055025 A1 | 3/2005 | Zacouto et al. |
| 2005/0060030 A1 | 3/2005 | Lashinski et al. |
| 2005/0075697 A1 | 4/2005 | Olson et al. |
| 2005/0209633 A1 | 9/2005 | Callister et al. |
| 2005/0222678 A1 | 10/2005 | Lashinski et al. |
| 2005/0240229 A1 | 10/2005 | Whitehurst et al. |
| 2005/0245957 A1 | 11/2005 | Starkebaum et al. |
| 2005/0261712 A1 | 11/2005 | Balbierz et al. |
| 2005/0266042 A1 | 12/2005 | Tseng |
| 2005/0267405 A1 | 12/2005 | Shah |
| 2005/0267596 A1 | 12/2005 | Chen et al. |
| 2006/0025855 A1 | 2/2006 | Lashinski et al. |
| 2006/0069414 A1 | 3/2006 | Imran et al. |
| 2006/0127246 A1 | 6/2006 | Forsell |
| 2006/0142635 A1 | 6/2006 | Forsell |
| 2006/0149124 A1 | 7/2006 | Forsell |
| 2006/0149129 A1 | 7/2006 | Watts et al. |
| 2006/0167539 A1 | 7/2006 | Mcewan |
| 2006/0212055 A1 | 9/2006 | Karabey et al. |
| 2006/0224177 A1 | 10/2006 | Finitsis |
| 2006/0229688 A1 | 10/2006 | McClure et al. |
| 2006/0235482 A1 | 10/2006 | Forsell |
| 2006/0257446 A1 | 11/2006 | Tropsha et al. |
| 2007/0015959 A1 | 1/2007 | Forsell |
| 2007/0038232 A1 | 2/2007 | Kraemer |
| 2007/0049790 A1 | 3/2007 | Wagner et al. |
| 2007/0073099 A1 | 3/2007 | Forsell |
| 2007/0092862 A1 | 4/2007 | Gerber |
| 2007/0156204 A1 | 7/2007 | Denker et al. |
| 2007/0167670 A1 | 7/2007 | Coleman et al. |
| 2007/0193632 A1 | 8/2007 | Shu |
| 2007/0204924 A1 | 9/2007 | Delgiacco et al. |
| 2007/0225802 A1 | 9/2007 | Forsell |
| 2007/0232848 A1 | 10/2007 | Forsell |
| 2007/0233019 A1 | 10/2007 | Forsell |
| 2007/0250020 A1 | 10/2007 | Kim et al. |
| 2007/0265675 A1 | 11/2007 | Lund et al. |
| 2008/0004487 A1 | 1/2008 | Haverfield |
| 2008/0045783 A1 | 2/2008 | Forsell |
| 2008/0051718 A1 | 2/2008 | Kavazov et al. |
| 2008/0086179 A1 | 4/2008 | Sharma |
| 2008/0103544 A1 | 5/2008 | Weiner |
| 2008/0154256 A1 | 6/2008 | Payne et al. |
| 2008/0178889 A1 | 7/2008 | Tal |
| 2008/0200753 A1 | 8/2008 | Forsell |
| 2008/0214888 A1 | 9/2008 | Shalom |
| 2008/0245371 A1 | 10/2008 | Gruber |
| 2008/0269548 A1 | 10/2008 | Vecchiotti et al. |
| 2008/0275296 A1 | 11/2008 | Forsell |
| 2009/0018388 A1 | 1/2009 | Forsell |
| 2009/0024108 A1 | 1/2009 | Lee-Sepsick et al. |
| 2009/0054725 A1 | 2/2009 | Forsell |
| 2009/0131959 A1 | 5/2009 | Rolland |
| 2009/0240100 A1 | 9/2009 | Forsell |
| 2009/0240294 A1 | 9/2009 | Forsell |
| 2009/0247817 A1 | 10/2009 | Forsell |
| 2009/0247818 A1 | 10/2009 | Forsell |
| 2009/0248033 A1 | 10/2009 | Forsell |
| 2009/0250068 A1 | 10/2009 | Forsell |
| 2009/0254106 A1 | 10/2009 | Forsell |
| 2009/0266366 A1 | 10/2009 | Swann et al. |
| 2010/0145138 A1 | 6/2010 | Forsell |
| 2010/0145139 A1 | 6/2010 | Forsell |
| 2010/0217067 A1 | 8/2010 | Forsell |
| 2010/0286735 A1 | 11/2010 | Garfield et al. |
| 2010/0312047 A1 | 12/2010 | Forsell |
| 2010/0312048 A1 | 12/2010 | Forsell |
| 2010/0312049 A1 | 12/2010 | Forsell |
| 2010/0312050 A1 | 12/2010 | Forsell |
| 2010/0312163 A1 | 12/2010 | Forsell |

| Publication No. | Date | Inventor |
|---|---|---|
| 2010/0312164 A1 | 12/2010 | Forsell |
| 2010/0312356 A1 | 12/2010 | Forsell |
| 2010/0318116 A1 | 12/2010 | Forsell |
| 2010/0318117 A1 | 12/2010 | Forsell |
| 2010/0318118 A1 | 12/2010 | Forsell |
| 2010/0324360 A1 | 12/2010 | Forsell |
| 2010/0324361 A1 | 12/2010 | Forsell |
| 2010/0324362 A1 | 12/2010 | Forsell |
| 2010/0324591 A1 | 12/2010 | Forsell |
| 2010/0331614 A1 | 12/2010 | Forsell |
| 2010/0331615 A1 | 12/2010 | Forsell |
| 2010/0331616 A1 | 12/2010 | Forsell |
| 2010/0331617 A1 | 12/2010 | Forsell |
| 2010/0331945 A1 | 12/2010 | Forsell |
| 2010/0332000 A1 | 12/2010 | Forsell |
| 2011/0009894 A1 | 1/2011 | Forsell |
| 2011/0009896 A1 | 1/2011 | Forsell |
| 2011/0009897 A1 | 1/2011 | Forsell |
| 2011/0015473 A1 | 1/2011 | Forsell |
| 2011/0015474 A1 | 1/2011 | Forsell |
| 2011/0040143 A1 | 2/2011 | Forsell |
| 2011/0172693 A1 | 7/2011 | Forsell |
| 2011/0184230 A1 | 7/2011 | Forsell |
| 2011/0192402 A1 | 8/2011 | Forsell |
| 2011/0196192 A1 | 8/2011 | Forsell |
| 2011/0196193 A1 | 8/2011 | Forsell |
| 2011/0196194 A1 | 8/2011 | Forsell |
| 2011/0196271 A1 | 8/2011 | Forsell |
| 2011/0196371 A1 | 8/2011 | Forsell |
| 2011/0196391 A1 | 8/2011 | Forsell |
| 2011/0196411 A1 | 8/2011 | Forsell |
| 2011/0196435 A1 | 8/2011 | Forsell |
| 2011/0196466 A1 | 8/2011 | Forsell |
| 2011/0196476 A1 | 8/2011 | Forsell |
| 2011/0196481 A1 | 8/2011 | Forsell |
| 2011/0196482 A1 | 8/2011 | Forsell |
| 2011/0196483 A1 | 8/2011 | Forsell |
| 2011/0196484 A1 | 8/2011 | Forsell |
| 2011/0196485 A1 | 8/2011 | Forsell |
| 2011/0196486 A1 | 8/2011 | Forsell |
| 2011/0196505 A1 | 8/2011 | Forsell |
| 2011/0196506 A1 | 8/2011 | Forsell |
| 2011/0201870 A1 | 8/2011 | Forsell |
| 2011/0201871 A1 | 8/2011 | Forsell |
| 2011/0201873 A1 | 8/2011 | Forsell |
| 2011/0202041 A1 | 8/2011 | Forsell |
| 2011/0202129 A1 | 8/2011 | Fofsell |
| 2011/0202131 A1 | 8/2011 | Forsell |
| 2011/0208231 A1 | 8/2011 | Forsell |
| 2011/0218394 A1 | 9/2011 | Forsell |
| 2011/0224787 A1 | 9/2011 | Forsell |
| 2011/0230930 A1 | 9/2011 | Forsell |
| 2011/0263928 A1 | 10/2011 | Forsell |

FOREIGN PATENT DOCUMENTS

| Country | Number | Date |
|---|---|---|
| EP | 0102548 | 3/1984 |
| EP | 01 343 40 | 3/1985 |
| EP | 0200286 | 11/1986 |
| EP | 0300552 | 1/1989 |
| EP | 0378251 | 7/1990 |
| EP | 0412191 | 2/1991 |
| EP | 0 583 012 | 2/1994 |
| EP | 0611561 | 9/1994 |
| EP | 0626154 A1 | 11/1994 |
| EP | 0876808 | 11/1998 |
| EP | 1 004 330 | 5/2000 |
| EP | 1 033 142 | 9/2000 |
| EP | 1072238 | 1/2001 |
| EP | 1514526 | 3/2005 |
| EP | 1563814 | 8/2005 |
| EP | 1563886 | 8/2005 |
| EP | 1 586 283 | 10/2005 |
| EP | 1598030 | 11/2005 |
| EP | 1 681 041 | 7/2006 |
| EP | 1 878 452 | 1/2008 |
| EP | 1 913 880 | 4/2008 |
| FR | 2688693 | 9/1993 |
| FR | 2692777 | 12/1993 |
| FR | 27565485 | 6/1998 |
| FR | 2797181 | 2/2001 |
| GB | 8 856 74 | 12/1961 |
| GB | 1194358 | 6/1970 |
| WO | 84/01282 | 4/1984 |
| WO | 94/27504 | 12/1994 |
| WO | 96/01597 | 1/1996 |
| WO | 96/11036 | 4/1996 |
| WO | WO 96/39932 | 12/1996 |
| WO | 97/41799 | 11/1997 |
| WO | WO 98/06358 | 2/1998 |
| WO | WO 98/50099 | 11/1998 |
| WO | 99/18885 | 4/1999 |
| WO | 00/09047 | 2/2000 |
| WO | 00/09048 | 2/2000 |
| WO | 00/15158 | 3/2000 |
| WO | WO 00/16686 | 3/2000 |
| WO | 0112078 | 2/2001 |
| WO | WO 01/12078 | 2/2001 |
| WO | WO 01/12108 | 2/2001 |
| WO | WO 01/45487 | 6/2001 |
| WO | WO 01/45590 | 6/2001 |
| WO | 01/47431 | 7/2001 |
| WO | 0147434 | 7/2001 |
| WO | 0147435 | 7/2001 |
| WO | WO 01/47575 | 7/2001 |
| WO | WO 0147439 | 7/2001 |
| WO | WO 01/58391 | 8/2001 |
| WO | WO 0154615 | 8/2001 |
| WO | WO 01/67964 | 9/2001 |
| WO | 02/40083 | 5/2002 |
| WO | WO 02/38217 | 5/2002 |
| WO | WO 02/053210 | 7/2002 |
| WO | WO 02/058563 | 8/2002 |
| WO | 02/087657 | 11/2002 |
| WO | WO 02/100481 | 12/2002 |
| WO | WO 03/002192 | 1/2003 |
| WO | WO 03/033054 | 4/2003 |
| WO | 2004/012806 | 2/2004 |
| WO | WO 2004/018037 | 3/2004 |
| WO | WO 2004/019765 | 3/2004 |
| WO | WO 2004/060171 | 7/2004 |
| WO | WO 2004/071684 | 8/2004 |
| WO | WO 2004/101029 | 11/2004 |
| WO | WO 2005/072169 | 8/2005 |
| WO | WO 2005/105003 | 11/2005 |
| WO | WO 2006/114004 | 11/2006 |
| WO | WO 2006/122285 | 11/2006 |
| WO | WO 2006/134106 | 12/2006 |
| WO | WO 2007/017880 | 2/2007 |
| WO | WO 2007/041795 | 4/2007 |
| WO | WO 2007/051563 | 5/2007 |
| WO | WO 2007/109759 | 9/2007 |
| WO | WO 2007/137026 | 11/2007 |
| WO | WO 2007/149555 | 12/2007 |
| WO | WO 2008/135988 | 11/2008 |
| WO | WO 2009/010799 | 1/2009 |
| WO | WO 2009/096854 | 8/2009 |
| WO | WO 2009/096865 | 8/2009 |
| WO | WO 2009/096868 | 8/2009 |
| WO | WO 2009/115645 | 9/2009 |

OTHER PUBLICATIONS

European Examination Report for EP 05 010 0460.0 dated May 19, 2006 (4 Pages).
Examination report dated Nov. 4, 2008 in European Patent App. No. 05010107.0.
European Search Report, dated Sep. 14, 2006, for EP 05010107.0.
International Preliminary Examination Report, completed May 3, 2002, for PCT/SE01/00268.
International Search Report for International Application PCT/SE01/00268, dated Jun. 25, 2001.
U.S. Appl. No. 09/373,224, filed Aug. 12, 1999, Forsell.
U.S. Appl. No. 11/988,450, filed May 27, 2009, Forsell.
Webster's II New River side University, 1984, pp. 573,1000.
Anand, Sneh. "Electrical Pacing of the Ampullary Isthmic Junction for Contraception", IEEE Engineering in Medicine & Biology 10th Annual International Conference, 1988.

* cited by examiner

IMPOTENCE TREATMENT APPARATUS WITH ENERGY TRANSFORMING MEANS

This application is a continuation application of U.S. application Ser. No. 10/203,085, filed Nov. 19, 2002, which is a U.S. national phase of International Application No. PCT/SE01/00268 filed Feb. 9, 2001 which designated the U.S. and claims priority to U.S. Provisional Application No's. 60/182,103, filed Feb. 11, 2000 and 60/182,104, filed Feb. 11, 2000, the entire contents of each of which are incorporated herein by reference.

The present invention relates to a male sexual impotence treatment apparatus, comprising an operable restriction device implantable in an impotent patient for engaging a tissue portion of the normal penile tissue or the prolongation thereof to form a restrictable penile exit blood flow passageway.

The expression "normal penile tissue or the prolongation thereof" should be understood to mean the penile tissue extended inside the human body and following the pathway of the blood flow leaving the penis i.e. one or more exit veins from the penis, the corpus cavernosum, crura or the prolongation thereof.

Male sexual impotence is a widespread problem. Many different solutions to this problem have been tried. A solution currently practiced is to replace the corpus cavernosa in the penis with a hydraulic inflatable/contractable silicon prosthesis, thus implanted in the penis. In fluid connection with this prosthesis is a reservoir implanted in the scrotum. By manual pumping action the prosthesis is filled with fluid from the reservoir to effect erect penile condition or is emptied of fluid, which returns to the reservoir, to effect flaccid penile condition. However, there are several more or less severe disadvantages of this solution. Above all, the penis is more or less damaged by the operation and it is practically impossible to reverse the operation. Another disadvantage is that rather strong forces act against this implanted prosthesis resulting in a significant risk of the prosthesis being broken.

Another solution to achieve erection is to restrict the blood flow leaving the penis. For example, U.S. Pat. Nos. 4,829,990, 4,958,630 and 5,048,511 disclose two hydraulically operated inflatable cuffs wrapped around respective crura or veins. A disadvantage of such a solution is that it involves complicated surgery. Another example on this solution is U.S. Pat. No. 4,828,544, which discloses an artificial fistula system surgically implanted and providing a primary fistula between the femoral artery and the femoral vein and a secondary fistula for leading blood from the primary fistula to the penis. The inflatable balloon engages the primary fistula between the secondary fistula and the vein. The balloon is in fluid connection with a manually compressible reservoir implanted in the scrotum. Again, implantation of this artificial fistula system requires delicate surgery. Yet another solution is to inject a substance in the penile vein system to achieve erection. However, injections are painful and complicated for the patient.

The object of the present invention is to provide a simple male sexual impotence treatment apparatus, which is conveniently controlled by the patient.

This object is obtained by an apparatus of the kind stated initially characterised by an energy transmission device for wireless transmission of energy from outside the patient's body to inside the patient's body for use in connection with the operation of the restriction device, including temporarily contracting said tissue portion to restrict the penile exit blood flow in the blood flow passageway to achieve erection.

As a result, the advantage is achieved that the impotence treatment apparatus of the invention provides simple and effective energy transmission which ensures an extended and reliable functionality of the apparatus, possibly for the rest of the patient's natural life, and at least many years.

The restriction device preferably controls the cross-sectional area of the passageway through which blood flow leaves the penis, which gives the advantage that the patient is enabled to adjust the restriction device to achieve the desired erection without feeling pain. This advantage should not be underestimated, because fine adjustments to restrict the cross-sectional area of the passageway, will allow maximal erection with minimum of restriction.

Generally, the apparatus comprises an energy transforming device implantable in the patient for transforming the energy wirelessly transmitted by the energy transmission device from a first form into a second form, preferably different than the first form.

The energy transforming device may comprise at least one semiconductor type of component or a circuitry of such semiconductor components. The semiconductor component may comprise a transistor or microchip or similar electronic components. However, the semiconductor component may not comprise rectifying diodes.

In accordance with a main embodiment of the invention, the energy transforming device comprises at least one element having a positive region and a negative region and adapted to create an energy field between the positive and negative regions when exposed to the energy of the first form transmitted by the energy transmission device, so that the energy field provides the energy of the second form. Typically, the above-mentioned semiconductor component may include such an element.

In accordance with a preferred embodiment of the invention, the element comprises an electrical junction element capable of inducing an electric field between the positive and negative regions when exposed to the energy of the first form transmitted by the energy transmission device, whereby the energy of the second form comprises electric energy.

Consequently, the restriction device suitably is electrically operated, whereby the positive and negative regions of the electrical junction element supply electric energy for the operation of the restriction device. The apparatus suitably comprises implantable electric conductors connected to the positive and negative regions of the electrical junction element, whereby the electrical junction element is capable of supplying an electric current, such as a direct current, a pulsating direct current, a combination of a direct and pulsating direct current, an alternating current or a combination of a direct and alternating current, via the conductors. Furthermore, the electrical junction element may be capable of supplying a frequency, amplitude, or frequency and amplitude modulated analog, digital, or a combination of analog and digital signal, which is used in connection with control of the restriction device.

The element, preferably in the form of an electrical semiconductor junction element, should be designed to generate an output current exceeding 1 μA when exposed to the energy of the first form transmitted by the energy transmission device. Suitably the electrical junction element forms a flat and thin sheet and has a volume of less than 2000 cm$^3$ to be suited for subcutaneous implantation, so that the electrical junction element can be located just behind the skin of the patient. Alternatively, it would be possible to implant the element in the thorax or cephalic region of the patient, or in an orifice of the patient's body and under the mucosa or intraluminar outside the mucosa of the orifice. Of course, all the components of the energy transforming device including the electrical junction element in contact with the patient's body should be of biocompatible material.

For in vitro appliances, a particular type of an electrical semiconductor junction element has been commonly used, namely a so-called p-n (positive/negative) junction element, typically in the form of solar cells. A solar cell transfers solar energy in the form of visible light into electric energy in the form of direct current. For example, a p-n junction element may comprise two layers of semiconductor, one p-type (positive) and the other n-type (negative), sandwiched together to form a "p-n junction". This p-n junction induces an electric field across the element when absorbing quanta of light (photons).

To be more precise, the quanta of light transfer their energy to some of the semiconductor's electrons, which are then able to move about through the material. For each such negatively charged electron, a corresponding positive charge—a "hole"—is created. In an ordinary semiconductor, these electrons and holes recombine after a short time and their energy is wasted as heat. However, when the electrons and holes are swept across the p-n junction in opposite directions by the action of the electric field, the separation of charge induces a voltage across the p-n junction element. By connecting the p-n junction element to an external circuit, the electrons are able to flow thereby creating a current.

Surprisingly, it has been proved that although both the skin and subcutis absorb energy from an external light beam directed against the skin portion behind which a properly designed p-n junction element is located, the light energy transmitted through the skin can induce a current from the p-n junction element strong enough (minimum 1 µA) to enable the operation of the electrically operated restriction device. Thus, such a p-n junction element is now for the first time used for in vivo applications.

The apparatus may comprise an implantable pulse generator for generating electrical pulses from the energy of the second form produced by the energy field.

Generally, the energy transforming device is adapted to transform the energy of the first form directly or indirectly into the energy of the second form.

In accordance with a preferred embodiment of the invention, the energy of the second form comprises electric energy and the energy transforming device comprises a capacitor, which may be adapted to produce electric pulses from the transformed electric energy. Preferably, the capacitor may be adapted to produce the pulses as the energy transforming device transforms the energy of the first form transmitted by the energy transmission device into the electric energy of the second form. The capacitor should be small to facilitate implantation thereof; i.e. its capacity may not be more than 0.1 µF.

The apparatus may comprise an implantable stabiliser for stabilising the energy of the second form. Where the energy of the second form comprises electric current the stabiliser may comprise at least one capacitor of the type described above.

In most embodiments of the invention, the apparatus comprises implantable electrical components. Where the electrical components include a capacitor of the type described above or an accumulator, at least one, preferably a single, voltage level guard may advantageously be provided, wherein the charge and discharge of the capacitor or accumulator is controlled by use of the voltage level guard. As a result, there is no need for any implanted current detector and/or charge level detector for the control of the capacitor, which makes the apparatus simple and reliable.

In a particular embodiment of the invention, the wireless energy of the first form comprises sound waves and the energy of the second form comprises electric energy, wherein the energy transforming device is adapted to directly transform the sound waves into electric energy.

The apparatus may comprise an implantable motor or pump for operating the restriction device, wherein the motor or pump is powered by the transformed energy.

In accordance with a main aspect of the invention, the energy transmission device may be adapted to transmit wireless energy for direct use in connection with the operation of the restriction device, as the wireless energy is being transmitted. The advantage of directly using energy as it is transmitted is that the apparatus can be of a very simple design and the few components involved makes the apparatus extremely reliable. For example, the energy transmission device may be adapted to directly power the motor or pump with wireless energy. The wireless energy may comprise a magnetic field or electromagnetic waves, suitably in the form of a signal, for direct power of the motor or pump. All the various functions of the motor and associated components described in the present specification may be used where applicable.

As an alternative to the above-noted main aspect of the invention, the energy transforming device may be adapted to supply the energy of the second form for direct use in connection with the operation of the restriction device, as the energy of the first form is being transformed into the energy of the second form. Consequently, the energy transforming device may be adapted to directly power the motor or pump with the energy of the second form.

Generally, the energy transforming device directly operates the restriction device with the energy of the second form in a non-magnetic, non-thermal or non-mechanical manner.

Where the apparatus comprises a motor, which may be adapted to directly or intermittently operate the restriction device, the energy transforming device may power the motor with the energy of the second form. Suitably, the restriction device is operable to perform a reversible function and the motor is capable of reversing said function.

In accordance with another embodiment of the invention, the restriction device comprises a hydraulic restriction device, and the apparatus comprises an implantable pump for operating the hydraulic restriction device, wherein the energy transforming device supplies the energy of the second form for driving the pump. Preferably, the pump is not a plunger type of pump, but may comprise a peristaltic or membrane pump.

The energy transforming device preferably is capable of generating as the energy of the second form a current exceeding 1 µA, when transferring the energy of the first form transmitted by the energy transmission device.

The apparatus may comprise an implantable adjustment device for adjusting the restriction device to change the restriction of the faecal passageway. In accordance with a first alternative the adjustment device is adapted to mechanically adjust the restriction device. In accordance with a second alternative the adjustment device is adapted to hydraulically adjust the restriction device by using implanted hydraulic means. Such hydraulic means may not use hydraulic fluid of the kind having a viscosity that substantially increases when exposed to heat or a magnetic field.

The apparatus of the present invention is not limited to the use of visible light for the wireless transmission of energy. Thus, in accordance with a broad aspect of the invention, the energy transmission device transmits energy by at least one wireless signal, preferably containing radiant energy.

The wireless signal may comprises a wave signal, for example an electromagnetic wave signal, such as an infrared light signal, a visible light signal, an ultra violet light signal, a laser signal, a micro wave signal, a radio wave signal, an x-ray radiation signal, and a gamma radiation signal. Where applicable, one or more of the above signals may be combined. Alternatively, the wave signal may comprise a sound wave signal, such as an ultrasonic signal. Generally, the wireless signal may comprise a digital, analog or a digital and analog signal.

The energy of the first form transmitted by the energy transmission device may comprise an electric or magnetic field transmitted in pulses, for example digital pulses. Furthermore, the energy transforming device may transform the energy of the first form, which may comprise polarised energy, into a direct current, pulsating direct current, a combination of a direct and pulsating direct current, an alternating current or a combination of a direct and alternating current. Alternatively, the energy of the first form may comprise kinetic energy.

The energy of the second form may comprise a frequency, amplitude or frequency and amplitude modulated analog, digital or combined analog and digital signal.

The restriction device may be non-inflatable, i.e. with no hydraulic fluid involved for the adjustments of the restriction device. This eliminates problems with fluid leaking from the restriction device.

The apparatus suitably comprises implantable electric conductors connected to the energy transforming device, whereby the energy transforming device is capable of supplying an electric current, such as direct current, a pulsating direct current, a combination of a direct and pulsating direct current, an alternating current or a combination of a direct and alternating current, via the conductors. Furthermore, the energy transforming device may be capable of supplying a frequency, amplitude, or frequency and amplitude modulated analog, digital, or a combination of analog and digital signal, which is used in connection with control of the restriction device.

In accordance with a main embodiment of the invention, the apparatus comprises an implantable operation device for operating the restriction device and a control device for controlling the operation device, wherein the energy transforming device powers the operation device with the energy of the second form. The operation device preferably comprises a motor, for example an electric linear motor or an electric rotary motor that is controlled by the control device to rotate a desired number of revolutions. Optionally, an implantable gearing may be connected to the motor. The electric motor may have electrically conductive parts made of plastics. Alternatively, the motor may comprise a hydraulic or pneumatic fluid motor, wherein the control device controls the fluid flow through the fluid motor. Motors currently available on the market are getting smaller and smaller. Furthermore, there is a great variety of control methods and miniaturised control equipment available. For example, the number of revolutions of a rotary motor may be analysed by a Hall-element just a few mm in size.

In accordance with another embodiment of the invention, the restriction device comprises hydraulic means and the operation device is adapted to conduct a hydraulic fluid in the hydraulic means. The operation device comprises a fluid conduit connected to the hydraulic means of the restriction device, and a reservoir for fluid, wherein the reservoir forms part of the conduit. The reservoir may form a fluid chamber with a variable volume, and the operation device may be adapted to distribute fluid from the chamber to the hydraulic means of the restriction device by reduction of the volume of the chamber and to withdraw fluid from the hydraulic means to the chamber by expansion of the volume of the chamber. The operation device suitably comprises an implantable motor used for reducing and expanding the volume of the chamber. Also, the operation device may comprise a pump for pumping the hydraulic fluid in the hydraulic means of the restriction device. All of the hydraulic components involved are preferably devoid of any non-return valve. This is of great advantage, because with valves involved there is always a risk of malfunction due to improperly working valves, especially when long time periods passes between valve operations.

The control device may be adapted to reverse the operation device by shifting polarity of the energy of the second form. Where the operation device comprises an electric motor the energy of the second form suitably comprises electric energy.

In accordance with yet another embodiment of the invention, the restriction device is operable to perform a reversible function, such as enlarging and restricting the blood flow passageway, and there is a reversing device implanted in the patient for reversing the function performed by the restriction device. Such a reversing function preferably involves enlarging and restricting the blood flow passageway by the restriction device, suitably in a stepless manner. In this connection, the control device suitably controls the reversing device, which may include a switch, to reverse the function performed by the restriction device. The reversing device may comprise hydraulic means including a valve for shifting the flow direction of a fluid in the hydraulic means. Alternatively, the reversing device may comprise a mechanical reversing device, such as a switch or a gearbox.

Where the reversing device comprises a switch it may be operable by the energy of the second form. In this case, the control device suitably controls the operation of the switch by shifting polarity of the energy of the second form supplied to the switch. The switch may comprise an electric switch and the source of energy may supply electric energy for the operation of the switch.

In accordance with an advantageous embodiment of the invention, the apparatus further comprises an energy storage device implanted in the patient for storing the energy of the second form and for supplying energy in connection with the operation of the restriction device. The implanted energy storage device preferably comprises an electric source of energy, such as an accumulator, a rechargeable battery or a combination of an accumulator and rechargeable battery.

The apparatus may further comprise a switch implantable in the patient for switching the operation of the restriction device and a source of energy implantable in the patient. This embodiment is particularly suited for applications where the energy transmission efficiency of the apparatus is insufficient, i.e. where the implanted restriction device is to perform more advanced operations. Such a source of energy preferably is a battery. Alternatively, the source of energy is an accumulator that also may store the energy of the second form.

In accordance with a first alternative, the switch is operated by the energy of the second form supplied by the energy storage device to switch from an off mode, in which the source of energy is not in use, to an on mode, in which the source of energy supplies energy for the operation of the restriction device. In this case, the implanted source of energy may comprise a battery, preferably having a lifetime of at least 10 years, or an accumulator. However, other kinds of sources are also conceivable, such as a nuclear source of energy or a chemical source of energy (fuel cells).

In accordance with a second alternative, the apparatus further comprises a remote control for controlling the supply of energy of the implanted source of energy, wherein the switch is operated by the energy of the second form supplied by the energy storage device to switch from an off mode, in which the remote control is prevented from controlling the source of energy and the source of energy is not in use, to a standby mode, in which the remote control is permitted to control the source of energy to supply energy for the operation of the restriction device.

In accordance with a third alternative, the energy storage device is omitted, wherein the switch is operated by the energy of the second form supplied by the energy transforming device to switch from an off mode, in which the remote control is prevented from controlling the source of energy and the source of energy is not in use, to a standby mode, in which the remote control is permitted to control the source of energy to supply energy for the operation of the restriction device.

In accordance with a fourth alternative, also the remote control is omitted, wherein the switch is operated by the energy of the second form supplied by the energy transforming device to switch from an off mode, in which the source of energy is not in use, to an on mode, in which the source of energy supplies energy for the operation of the restriction device. Where applicable, in the described embodiments the switch may switch when the energy transmission device is transmitting wireless energy, preferably while the transferred energy of the second form is stabilised by an implanted capacitor, which may temporarily (for a few seconds) store the energy of the second form.

In the above noted third and fourth alternatives, the energy transmission device may be substituted for the energy transforming device, whereby the switch is operated by the energy of the first form.

The switch mentioned above may comprise an electronic switch or, where applicable, a mechanical switch.

The advantage of using a switch above all is increased control safety; i.e. interfering signals in the patient's surroundings cannot affect the implanted restriction device. Furthermore, the lifetime of the implanted source of energy will be significantly prolonged, since the energy consumption of the apparatus will be reduced to a minimum. During the above-mentioned standby mode, the remote control uses energy from the implanted source of energy. By means of the energy transmission device energy may be transmitted to activate the switch to connect the implanted source of energy only when energy is required in connection with the operation of the restriction device.

All of the above embodiments may be combined with at least one implantable sensor for sensing at least one physical parameter of the patient, wherein the control device may control the restriction device in response to signals from the sensor. Advantageously, the sensor may sense ejaculation, and the restriction device may release said tissue portion in response to the sensor sensing ejaculation.

The control device may comprise an internal control unit implantable in the patient for, preferably directly, controlling the restriction device in response to signals from the sensor. In response to signals from the sensor, for example signals related to pressure, the patient's position or any other important physical parameter, the internal control unit may send information thereon to outside the patient's body. The control device may also automatically control the restriction device in response to signals from the sensor. For example, the control device may control the restriction device to further restrict the blood flow passageway in response to the sensor sensing that the patients blood flow and blood pressure are increasing, or enlarge the blood flow passageway in response to the sensor sensing an abnormally high pressure against the restriction device or sensing ejaculation.

Alternatively, the control device may comprise an external control unit outside the patient's body for, suitably directly, controlling the restriction device in response to signals from the sensor. The external control unit may store information on the physical parameter sensed by the sensor and may be manually operated to control the restriction device based on the stored information. In addition, there may be at least one implantable sender for sending information on the physical parameter sensed by the sensor.

An external data communicator may be provided outside the patient's body and an internal data communicator may be implanted in the patient for communicating with the external communicator. The internal communicator may feed data related to the patient, or related to the restriction device, back to the external communicator. Alternatively or in combination, the external communicator may feed data to the internal communicator. The internal communicator may suitably feed data related to at least one physical signal of the patient.

The apparatus may further comprise an implantable programmable control unit for controlling the restriction device, preferably over time in accordance with an activity schedule program. This will advance the apparatus and make possible an adaptation of the apparatus to the individual patients.

Many of the above embodiments are suitably remote controlled. Thus, the apparatus advantageously comprises a wireless remote control transmitting at least one wireless control signal for controlling the restriction device. With such a remote control it will be possible to adapt the function of the apparatus to the patient's need. The control signal may comprise a frequency, amplitude or frequency or amplitude modulated signal. Furthermore, the control signal may comprise an analog or a digital signal, or a combination of an analog and digital signal.

The wireless remote control may be capable of obtaining information on the condition of the implanted restriction device and of controlling the restriction device in response to the information. Also, The remote control may be capable of sending information related to the restriction device from inside the patient's body to the outside thereof.

In a particular embodiment of the invention, the wireless remote control comprises at least one external signal transmitter or transceiver and at least one internal signal receiver or transceiver implantable in the patient. In another particular embodiment of the invention, the wireless remote control comprises at least one external signal receiver or transceiver and at least one internal signal transmitter or transceiver implantable in the patient.

The wireless remote control may transmit a carrier signal for carrying the control signal, wherein the carrier signal is frequency, amplitude or frequency and amplitude modulated. The carrier signal may also comprise digital, analog or a combination of digital and analog signals. Such signals may comprise wave signals. Also the control signal used with the carrier signal may be frequency, amplitude or frequency and amplitude modulated, and be digital, analog or combined digital and analog.

The control signal may comprise a wave signal, for example, a sound wave signal, such as an ultrasound wave signal, an electromagnetic wave signal, such as an infrared light signal, a visible light signal, an ultra violet light signal, a laser signal, a micro wave signal, a radio wave signal, an x-ray radiation signal, or a gamma radiation signal. Where applicable, two or more of the above signals may be combined.

The control signal may be digital or analog, and may comprise an electric or magnetic field. Suitably, the wireless remote control may transmit an electromagnetic carrier wave signal for carrying the digital or analog control signal. For example, use of an analog carrier wave signal carrying a digital control signal would give safe communication. The control signal may be transmitted in pulses by the wireless remote control.

The energy transmission device may function different from or similar to the energy transforming device. For example, the energy transmission and transforming devices function differently when the energy transmission device comprises a coil used for transmitting the energy of the first form and the energy transforming device comprises an electrical junction element for transforming the transmitted energy into the energy of the second form. The energy transmission and transforming devices function similar to each other when the energy transmission device comprises a coil used for transmitting the energy of the first form and the energy transforming device also comprises a coil for transforming the transmitted energy into the energy of the second form.

In accordance with an alternative embodiment of the invention, the apparatus comprises an activatable source of energy implantable in the patient, wherein the source of energy is activated by wireless energy transmitted by the energy transmission device, to supply energy which is used in connection with the operation of the restriction device.

The implantable restriction device suitably is embedded in a soft or gel-like material. For example, a silicone material having hardness less than 20 Shore.

All the above described various components, such as the motor, pump and capacitor, may be combined in the different embodiments where applicable. Also the various functions described in connection with the above embodiments of the invention may be used in different applications, where applicable.

All the various ways of transferring, transforming and controlling energy presented in the present specification may be practised by using all of the various components and solutions described.

The present invention also provides methods for implanting the apparatus of the invention, and for treating impotence.

Accordingly, there is provided an implanting method, comprising the steps of: providing an impotence treatment apparatus as described above, cutting an opening in a patient's mucosa in the orifice of the patient's body, and implanting the energy transforming means in the patient's body through the opening. Alternatively, the cutting step may comprise cutting the opening in the patient's skin and the implanting step may comprise implanting the energy transforming means in the patient's body through the opening.

There is also provided a laparascopical implanting method, comprising the steps of: providing the impotence treatment apparatus as described above, placing at least two laparascopic cannula within a patient's body, and implanting the energy transforming means in the patient's body by using the at least two laparoscopic cannula.

In accordance with another alternative there is provided a laparascopical surgical method of implanting the impotence treatment apparatus, comprising the steps of: a) Providing the impotence treatment apparatus as described above. b) Placing at least two laparoscopic trocars within the patient's body. c) Using a dissecting tool inserted through the laparoscopic trocars, dissecting the region of the penile tissue or the prolongation thereof. d) Introducing the operable restriction device of the apparatus through the trocars. e) Placing the restriction device in engagement with the penile tissue or the prolongation thereof to create a stoma through which blood flow leaves the penis. And f) implanting the energy transforming means of the apparatus in the patient for transforming wireless energy into energy of a form suited for operating the restriction device to reduce the stoma to restrict the blood flow therethrough. The method as recited in (a)-(f) may further comprise adjusting the reduced stoma in a non-invasive procedure.

There is also provided a method of treating an impotent male comprising: (a) Surgically implanting in a male patient a restriction device engaging the male's penile tissue or the prolongation thereof to form a restrictable passageway in which blood flow leaves the penis. (b) Surgically implanting in the male the operation device which can adjust the restricted passageway in response to supplied energy. And (c) in a non-invasive post-operative procedure, from time to time, supplying energy to the operation device so as to restrict the passageway to reduce the blood flow leaving the male's penis to achieve erection. In the method (c) may be practised by the patient whenever he desires.

The invention is described in more detail in the following with reference to the accompanying drawings, in which FIGS. 1 to 12 are schematic block diagrams illustrating twelve embodiments, respectively, of the male sexual impotence treatment apparatus of the invention, in which wireless energy is transmitted from outside a patient's body to energy consuming components of the apparatus implanted in the patient;

Referring to the drawing figures, like reference numerals designate identical or corresponding elements throughout the several figures.

Figure 1:
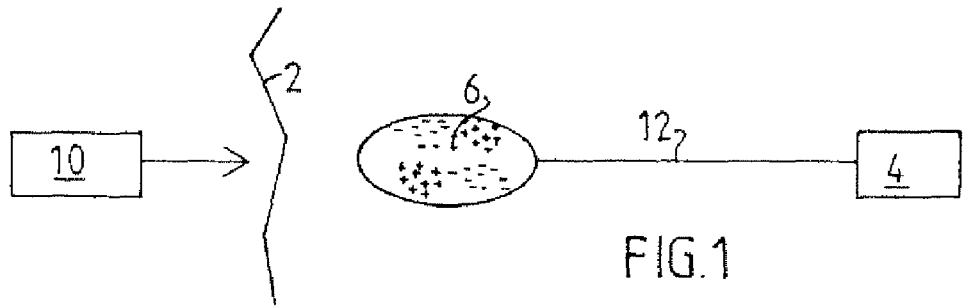

FIG. 1 schematically shows a very simple embodiment of the impotence apparatus of the invention having some parts implanted in a patient and other parts located outside the patient's body. Thus, in FIG. 1 all parts placed to the right of the patient's skin 2 are implanted and all parts is placed to the left of the skin 2 are located outside the patient's body.

The apparatus of FIG. 1 comprises an implanted operable restriction device 4, which engages penile tissue or the prolongation thereof to form a restrictable passageway for blood flow leaving the penis. The restriction device 4 is capable of performing a reversible function, i.e. to enlarge and restrict the passageway, so that the restriction device 4 works as an artificial sphincter. The implanted energy transforming means 6 is adapted to supply energy consuming components of the restriction device 4 with energy via a power supply line 12. The external energy transmission means 10 includes a wireless remote control transmitting a wireless signal which is received by a signal receiver incorporated in the implanted energy transforming means 6. The implanted energy transforming means 6 transforms energy from the signal into electric energy which is supplied via the power supply line 12 to the restriction device 4, which energy causes portions of the device 4 to move and thus adjust the opening.

Figure 2:
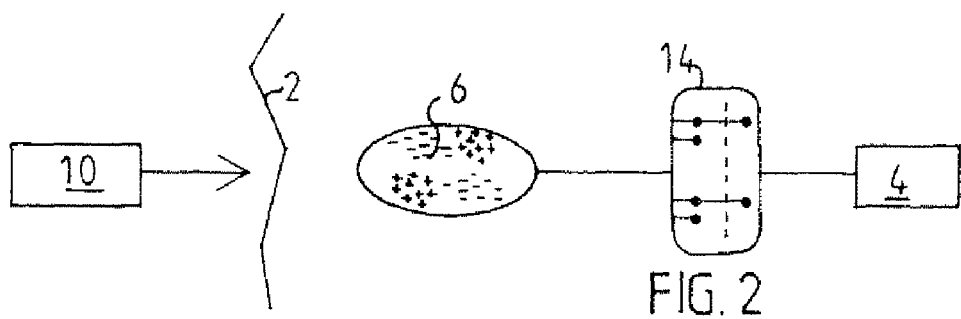

FIG. 2 shows an embodiment of the invention identical to that of FIG. 1, except that a reversing device in the form of an electric switch 14 also is implanted in the patient for reversing the restriction device 4. The wireless remote control of the external energy transmission means 10 transmits a wireless signal that carries energy and the implanted energy transforming means 6 transforms the wireless energy into a current for operating the switch 14. When the polarity of the current is shifted by the energy transforming means 6 the switch 14 reverses the function performed by the restriction device 4.

Figure 3:
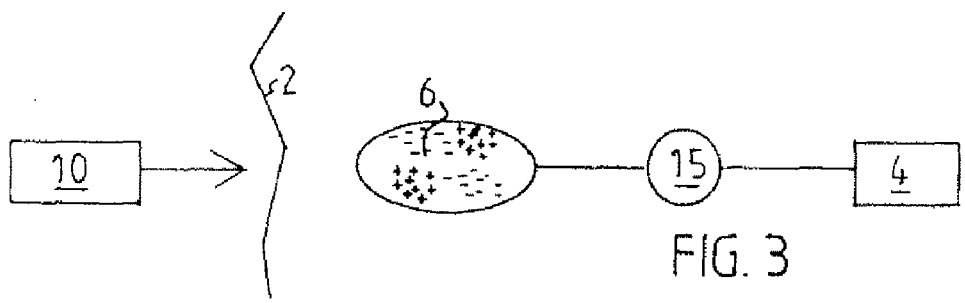

FIG. 3 shows an embodiment of the invention identical to that of FIG. 1, except that the operation device in the form of a motor 15 for operating the restriction device 4 also is implanted in the patient. The motor 15 is powered with energy from the energy transforming means 6, as the remote control of the external energy transmission means 10 transmits a wireless signal to the receiver of the energy transforming means 6.

Figure 4:
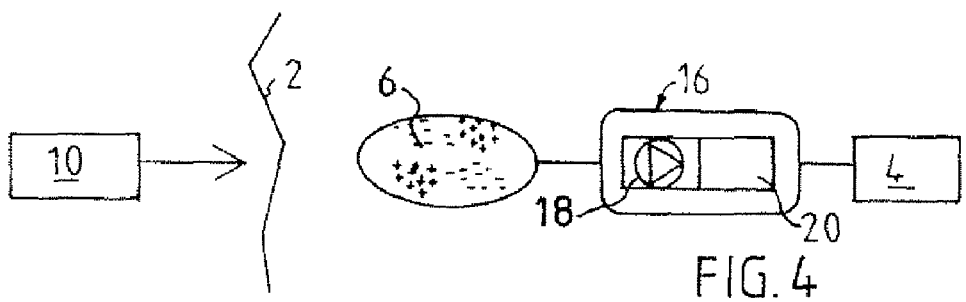

FIG. 4 shows an embodiment of the invention identical to that of FIG. 1, except that an assembly 16 including a motor/pump unit 18 and a fluid reservoir 20 also is implanted in the patient. In this case the restriction device 4 is hydraulically operated, i.e. hydraulic fluid is pumped by the motor/pump unit 18 from the reservoir 20 through a conduit 22 to the restriction device 4 to restrict the passageway, and hydraulic fluid is pumped by the motor/pump unit 18 back from the restriction device 4 to the reservoir 20 to enlarge the cross-sectional area. The implanted energy transforming means 6 transforms wireless energy into a current, for powering the motor/pump unit 18 via the electric power supply line 24.

Figure 5:
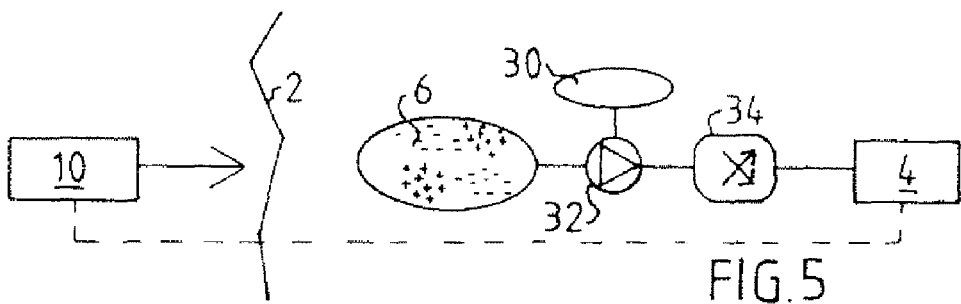

FIG. 5 shows an embodiment of the invention comprising the external energy transmission means 10 with its wireless remote control, the restriction device 4, in this case hydraulically operated, and the implanted energy transforming means 6, and further comprising an implanted hydraulic fluid reservoir 30, an implanted motor/pump unit 32 and an implanted reversing device in the form of a hydraulic valve shifting device 34. The motor of the motor/pump unit 32 is the electric motor. In response to a control signal from the wireless remote control of the external energy transmission means 10, the implanted energy transforming means 6 powers the motor/pump unit 32 with energy from the energy carried by the control signal, whereby the motor/pump unit 32 distributes hydraulic fluid between the reservoir 30 and the restriction device 4. The remote control of the energy transmission means controls the shifting device 34 to shift the hydraulic fluid flow direction between one direction in which the fluid is pumped by the motor/pump unit 32 from the reservoir 30 to the restriction device 4 to reduce the passageway, and another opposite direction in which the fluid is pumped by the motor/pump unit 32 back from the restriction device 4 to the reservoir 30 to enlarge the cross-sectional area.

Figure 6:
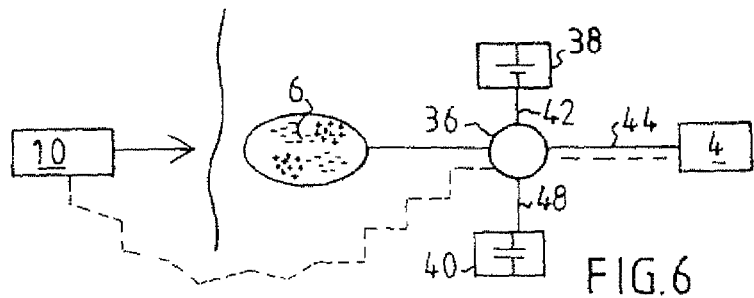

FIG. 6 shows an embodiment of the invention identical to that of FIG. 1, except that a control unit 36 controlled by the wireless remote control of the external energy transmission means 10, an accumulator 38 and a capacitor 40 also are implanted in the patient. The control unit 36 stores electric energy received from the energy transforming means 6 in the accumulator 38, which supplies energy to the restriction device 4. In response to a control signal from the wireless remote control of the energy transmission means 10, the control unit 6 either releases electric energy from the accumulator 38 and transfers the released energy via power lines 42 and 44, or directly transfers electric energy from the energy transforming means 6 via a power line 46, the capacitor 40, which stabilises the electric current, a power line 48 and the power line 44, for the operation of the restriction device 4.

In accordance with one alternative, the capacitor 40 in the embodiment of FIG. 6 may be omitted. In accordance with another alternative, the accumulator 38 in this embodiment may be omitted.

Figure 7:
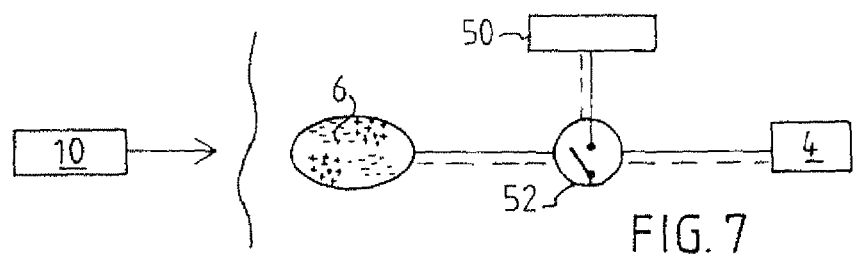

FIG. 7 shows an embodiment of the invention identical to that of FIG. 1, except that a battery 50 for supplying energy for the operation of the restriction device 4 and an electric switch 52 for switching the operation of the restriction device 4 also are implanted in the patient. The switch 52 is operated by the energy supplied by the energy transforming means 6 to switch from an off mode, in which the battery 50 is not in use, to an on mode, in which the battery 50 supplies energy for the operation of the restriction device 4.

Figure 8:
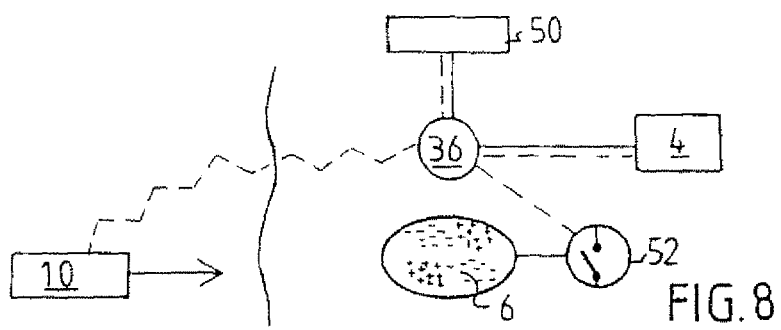

FIG. 8 shows an embodiment of the invention identical to that of FIG. 7, except that a control unit 36 controllable by the wireless remote control of the external energy transmission means 10 also is implanted in the patient. In this case, the switch 52 is operated by the energy supplied by the energy transforming means 6 to switch from an off mode, in which the wireless remote control is prevented from controlling the control unit 36 and the battery 50 is not in use, to a standby mode, in which the remote control is permitted to control the control unit 36 to release electric energy from the battery 50 for the operation of the restriction device 4.

Figure 9:
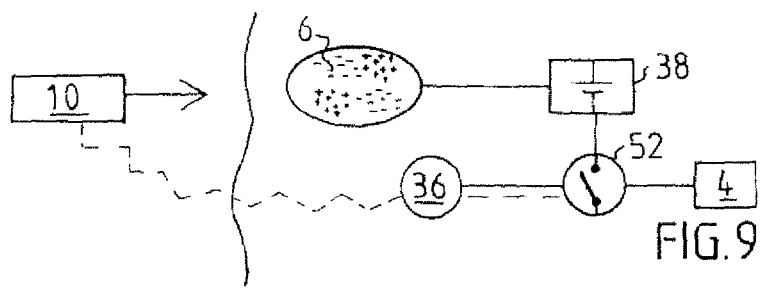

FIG. 9 shows an embodiment of the invention identical to that of FIG. 8, except that the accumulator 38 is substituted for the battery 50 and the implanted components are interconnected differently. In this case, the accumulator 38 stores energy from the energy transforming means 6. In response to a control signal from the wireless remote control of the external energy transmission means 10, the implanted control unit 36 controls the switch 52 to switch from an off mode, in which the accumulator 38 is not in use, to an on mode, in which the accumulator 38 supplies energy for the operation of the restriction device 4.

Figure 10:
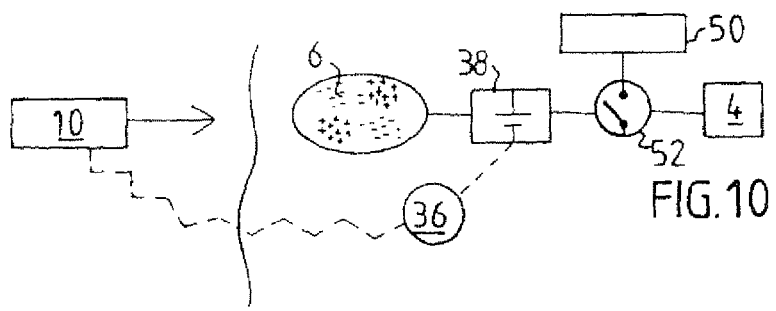

FIG. 10 shows an embodiment of the invention identical to that of FIG. 9, except that the battery 50 also is implanted in the patient and the implanted components are interconnected differently. In response to a control signal from the wireless remote control of the external energy transmission means 10, the implanted control unit 35 controls the accumulator 38 to deliver energy for operating the switch 52 to switch from an off mode, in which the battery 50 is not in use, to an on mode, in which the battery 50 supplies electric energy for the operation of the restriction device 4.

Alternatively, the switch 52 may be operated by energy supplied by the accumulator 38 to switch from an off mode, in which the wireless remote control is prevented from controlling the battery 50 to supply electric energy and the battery 50 is not in use, to a standby mode, in which the wireless remote control is permitted to control the battery 50 to supply electric energy for the operation of the restriction device 4.

Figure 11:
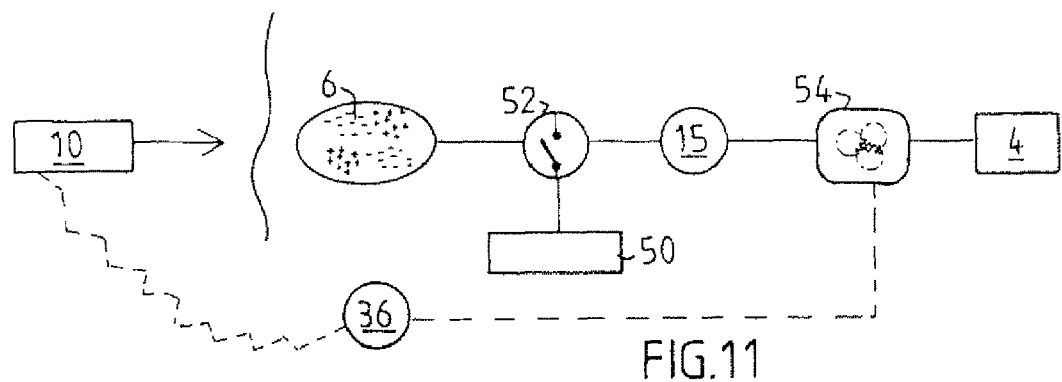

FIG. 11 shows an embodiment of the invention identical to that of FIG. 7, except that a motor 15, a mechanical reversing device in the form of a gearbox 54 and a control unit 36 for controlling the gearbox 54 also are implanted in the patient. The implanted control unit 36 controls the gearbox 54 to reverse the function performed by the restriction device 4 (mechanically operated).

Figure 12:
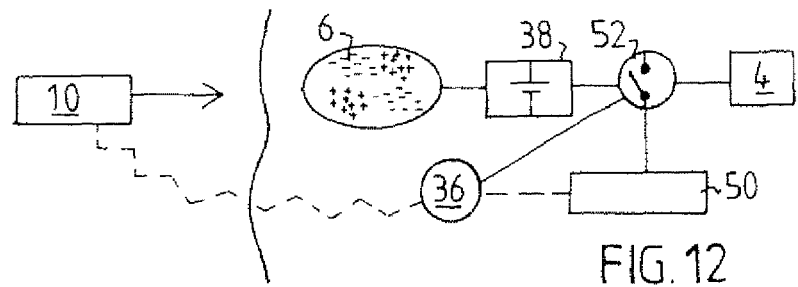

FIG. 12 shows an embodiment of the invention identical to that of FIG. 10 except that the implanted components are interconnected differently. Thus, in this case the battery 50 powers the control unit 36 when the accumulator 38, suitably a capacitor, activates the switch 52 to switch to an on mode.

When the switch 52 is in its on mode the control unit 36 is permitted to control the battery 50 to supply, or not supply, energy for the operation of the restriction device 4.

Figure 13:
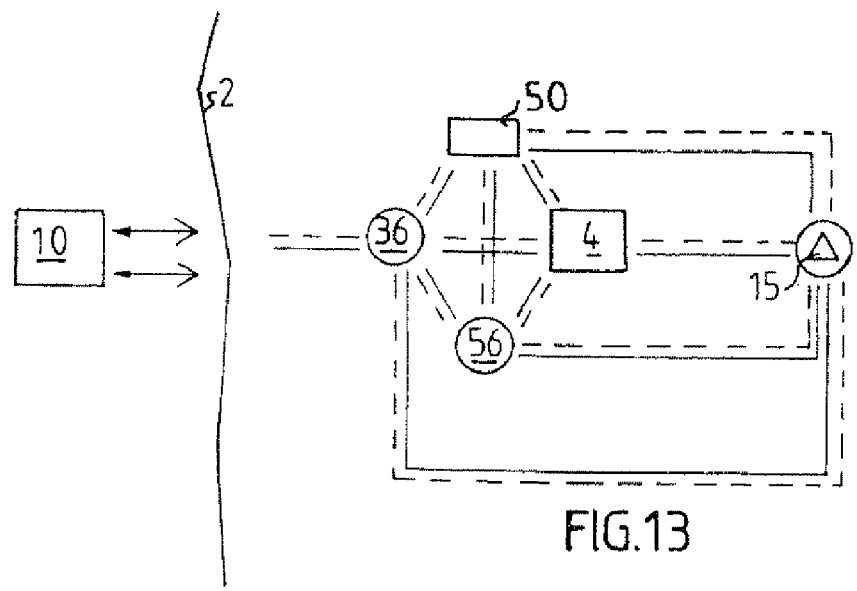
FIG. 13 is a schematic block diagram illustrating conceivable combinations of implanted components for achieving various communication options.

FIG. 13 schematically shows conceivable combinations of implanted components of the apparatus for achieving various communication options. Basically, there are the implanted restriction device 4, control unit 36 and motor/pump unit 18, and the external energy transmission means 10 including the external wireless remote control. As already described above the wireless remote control transmits a control signal which is received by the implanted control unit 36, which in turn controls the various implanted components of the apparatus.

A sensor 56 may be implanted in the patient for sensing a physical parameter of the patient, such as the pressure in the passageway. The implanted control unit 36, or alternatively the external wireless remote control of the energy transmission means 10, may control the restriction device 4 in response to signals from the sensor 56. A transceiver may be combined with the sensor 56 for sending information on the sensed physical parameter to the external wireless remote control. The wireless remote control may comprise a signal transmitter or transceiver and the implanted control unit 36 may comprise a signal receiver or transceiver. Alternatively, the wireless remote control may comprise a signal receiver or transceiver and the implanted control unit 36 may comprise a signal transmitter or transceiver. The above transceivers, transmitters and receivers may be used for sending information or data related to the restriction device 4 from inside the patient's body to the outside thereof.

Where the motor/pump unit 18 and battery 50 for powering the motor/pump unit 18 are implanted, the battery 50 may be equipped with a transceiver for sending information on the condition of the battery 50.

Those skilled in the art will realise that the above various embodiments according to FIGS. 1-13 could be combined in many different ways. For example, the energy operated switch 14 could be incorporated in any of the embodiments of FIGS. 3,6-12, the hydraulic shifting device 34 could be incorporated in the embodiment of FIG. 4, and the gearbox 54 could be incorporated in the embodiment of FIG. 3.

Figure 14:
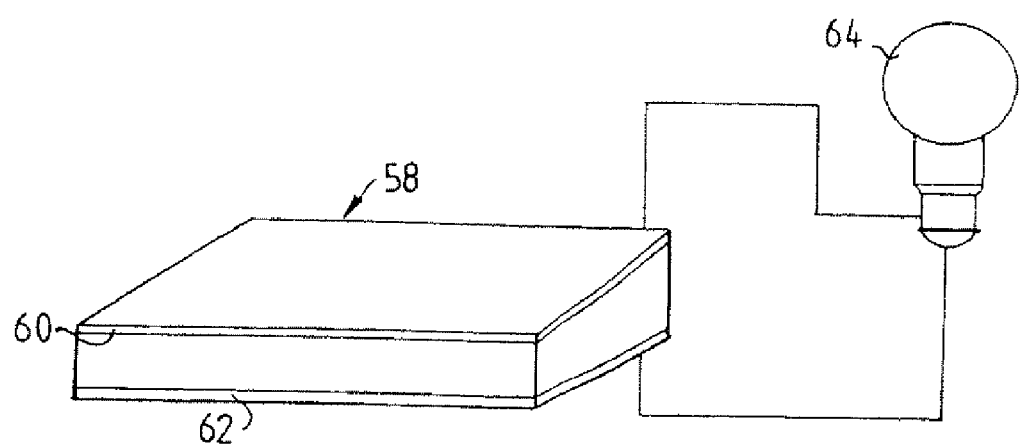
FIG. 14 illustrates an electrical junction element for use in the apparatus of the present invention.

FIG. 14 shows the energy transforming means in the form of an electrical junction element 58 for use in any of the above embodiments according to FIGS. 1-13. The element is a flat p-n junction element comprising a p-type semiconductor layer 60 and an n-type semiconductor layer 62 sandwiched together. A light bulb 64 is electrically connected to opposite sides of the element 58 to illustrate how the generated current is obtained. The output of current from such a p-n junction element 58 is correlated to the temperature. See the formula below.

$$I = I0(\exp(qV/kT) - 1)$$

where

I is the external current flow,

I0 is the reverse saturation current, q is the fundamental electronic charge of 1.602×10-19 coulombs, V is the applied voltage, k is the Boltzmann constant, and T is the absolute temperature.

Under large negative applied voltage (reverse bias), the exponential term becomes negligible compared to 1.0, and I is approximately −I0. I0 is strongly dependent on the temperature of the junction and hence on the intrinsic-carrier concentration. I0 is larger for materials with smaller bandgaps than for those with larger bandgaps. The rectifier action of the diode, that is, its restriction of current flow to only one direction, is in this particular embodiment the key to the operation of the p-n junction element 58.

The alternative way to design a p-n junction element is to deposit a thin layer of semiconductor onto a supporting material which does not absorb the kind of energy utilised in the respective embodiments. For use with wirelessly transmitted energy in terms of light waves, glass could be a suitable material. Various materials may be used in the semiconductor layers such as but not limited to cadmium telluride, copper-indium-diselenide and silicon. It is also possible to use a multilayer structure with several layers of p and n-type materials to improve efficiency.

The electric energy generated by the p-n junction element 58 could be of the same type as generated by solar cells, in which the negative and positive fields create a direct current. Alternatively, the negative and positive semiconductor layers may change polarity following the transmitted waves, thereby generating the alternating current.

The p-n junction element 58 is designed to make it suited for implantation. Thus, all the external surfaces of the element 58 in contact with the human body are made of a biocompatible material. The p-n junction semiconductors are designed to operate optimally at a body temperature of 37° C. because the current output, which should be more than 1 μA, is significantly depending on temperature as shown above. Since both the skin and subcutis absorb energy, the relation between the sensitivity or working area of the element 58 and the intensity or strength of the wireless energy transmission is considered. The p-n junction element 58 preferably is designed flat and small. Alternatively, if the element 58 is made in larger sizes it should be flexible, in order to adapt to the patient's body movements. The volume of the element 58 should be kept less than 2000 cm$^3$.

Figure 15:
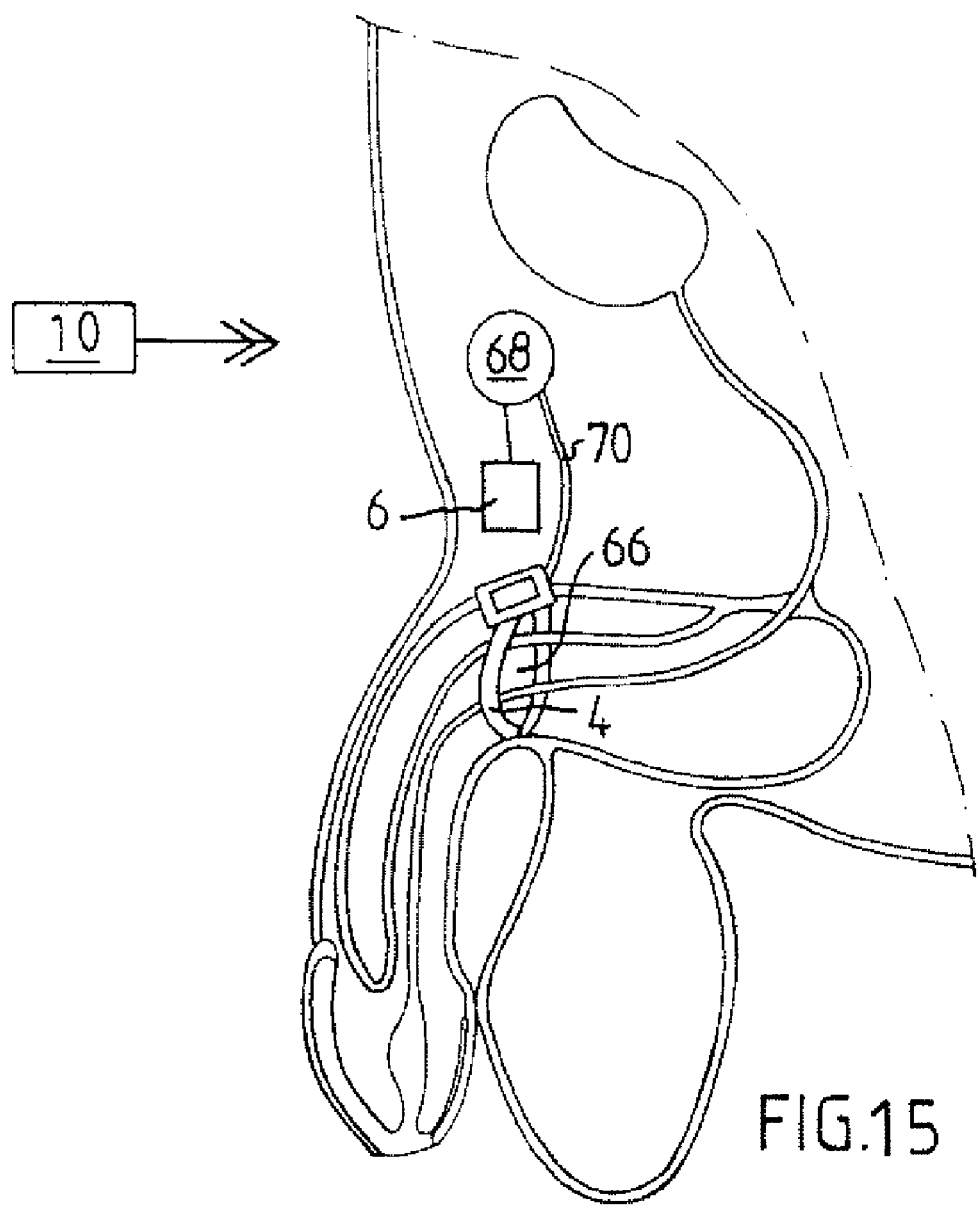
FIG. 15 illustrates the apparatus in accordance with the invention implanted in a patient.

FIG. 15 generally illustrates how any of the above-described embodiments of the impotence treatment apparatus of the invention may be implanted in a male patient. Thus, a restriction device 4 implanted in a patient engages penile tissue or the prolongation thereof to form an artificial sphincter around the passageway through which the blood flow leaves the penis. An implanted operation device 68, which may also be referred to as an adjustment device, such as an electric motor or a motor/pump assembly, operates the restriction device 4 through a transmission member 70, such as a mechanical transmission cord or a fluid tube. The energy transforming means in the form of the element 6 having a positive region and a negative region, as described above in more detail, is placed underneath the skin of the patient. The external energy transmission means 10 is adapted to transmit wireless energy to the implanted element 6. A wireless remote control includes an external control unit incorporated in the energy transmission means 10, and an implanted control unit 71 connected to the element 6 and the operation device 68.

Wireless energy carried by a signal transmitted by the wireless remote control of the external energy transmission means 10 at least partly penetrates the patient's skin and hits the element 6. The energy thus hitting the element 6 is transformed into energy of a different form that is suited for powering the operation device 68. For example, where the operation device 68 is an electric motor the element 6 comprises an electric p-n junction element that transforms the wireless energy into an electric current for powering the electric motor. Where the operation device 68 comprises a pump, the element 6 may transform the wireless energy into kinetic energy for powering the pump.

The transformed energy may be utilised for directly operating the restriction device 4 or, where the restriction device 4 is electrically operated, for storage in a capacitor and/or an accumulator for later or parallel use. Preferably (but not necessarily) the element 6 is controlled by a microprocessor. The wireless remote control of the external energy transmission means 10 is used to control the utilisation of the transmitted energy and any function or command to/from the implanted restriction device 4.

Figure 16:
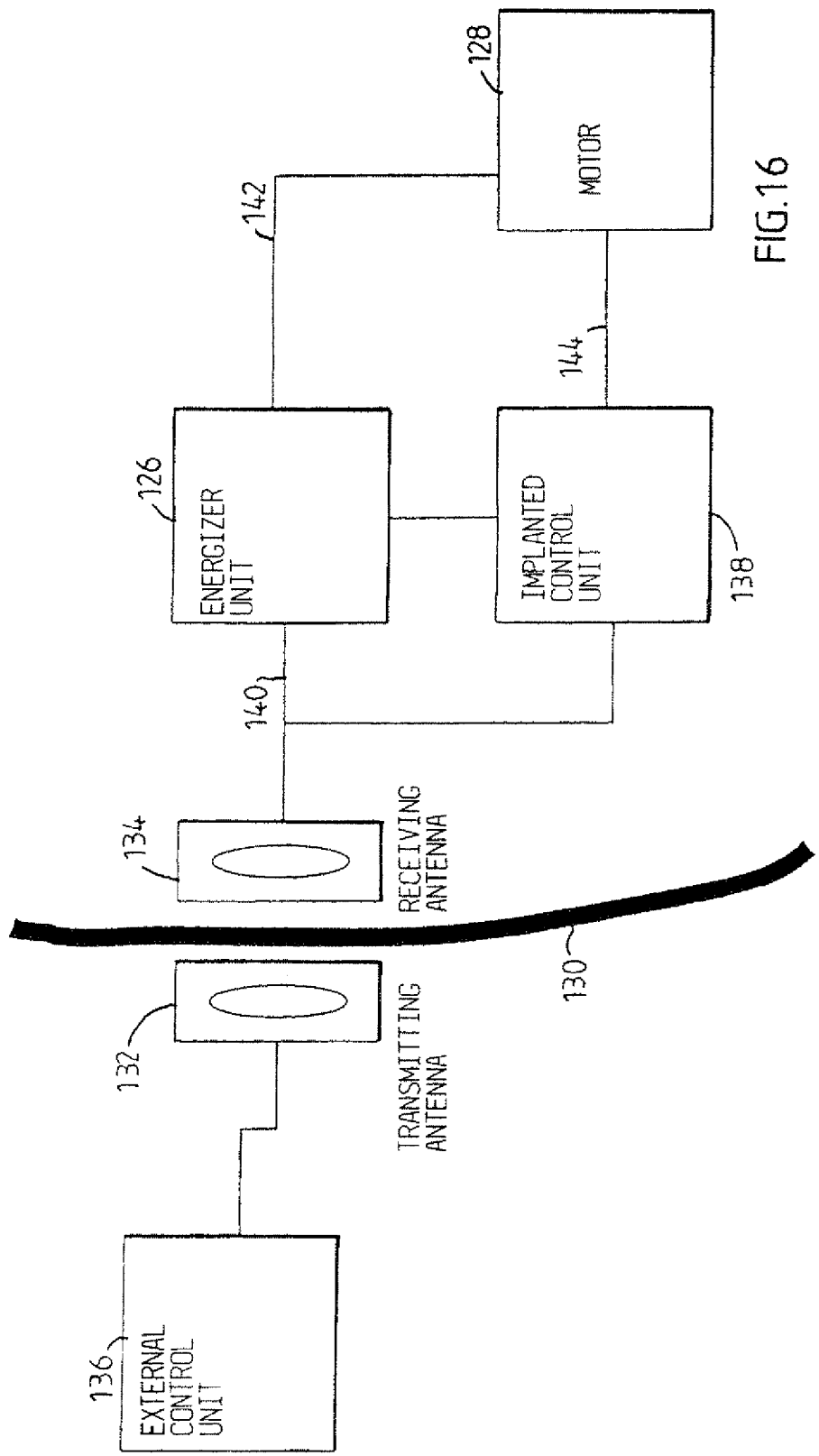
FIG. 16 is a block diagram illustrating remote control components of an embodiment of the invention, in which wireless energy is transmitted by the use of electromagnetic signals.

FIG. 16 shows the basic parts of a wireless remote control of the apparatus of the invention including an electric motor 128 for operating a restriction member, for example of the type illustrated in FIG. 15. In this case, the remote control is based on the transmission of electromagnetic wave signals, often of high frequencies in the order of 100 kHz-1 gHz, through the skin 130 of the patient. In FIG. 15, all parts placed to the left of the skin 130 are located outside the patient's body and all parts placed to the right of the skin 130 are implanted. Any suitable remote control system may be used.

An external signal transmitting antenna 132 is to be positioned close to a signal receiving antenna 134 implanted close to the skin 130. As an alternative, the receiving antenna 134 may be placed for example inside the abdomen of the patient. The receiving antenna 134 comprises a coil, approximately 1-100 mm, preferably 25 mm in diameter, wound with a very thin wire and tuned with a capacitor to a specific high frequency. A small coil is chosen if it is to be implanted under the skin of the patient and a large coil is chosen if it is to be implanted in the abdomen of the patient. The transmitting antenna 132 comprises a coil having about the same size as the coil of the receiving antenna 134 but wound with a thick wire that can handle the larger currents that is necessary. The coil of the transmitting antenna 132 is tuned to the same specific high frequency as the coil of the receiving antenna 134.

An external control unit 136 comprises a microprocessor, a high frequency electromagnetic wave signal generator and a power amplifier. The microprocessor of the control unit 136 is adapted to switch the generator on/off and to modulate signals generated by the generator to send digital information via the power amplifier and the antennas 132,134 to an implanted control unit 138. To avoid that accidental random high frequency fields trigger control commands, digital signal codes are used. A conventional keypad placed on the external control unit 136 is connected to the microprocessor thereof. The keypad is used to order the microprocessor to send digital signals to either contract or enlarge the restriction device. The microprocessor starts a command by applying a high frequency signal on the antenna 132. After a short time, when the signal has energised the implanted parts of the control system, commands are sent to contract or enlarge the restriction device in predefined steps. The commands are sent as digital packets in the form illustrated below.

| Start pattern, | Command, | Count, | Checksum, |
|---|---|---|---|
| 8 bits | 8 bits | 8 bits | 8 bits |

The commands are sent continuously during a rather long time period (e.g. about 30 seconds or more). When a new contract or enlarge step is desired the Count byte is increased by one to allow the implanted control unit 138 to decode and understand that another step is demanded by the external control unit 136. If any part of the digital packet is erroneous, its content is simply ignored.

Through a line 140, an implanted energiser unit 126 draws energy from the high frequency electromagnetic wave signals received by the receiving antenna 134. The energiser unit 126 stores the energy in an energy storage device, such as a large capacitor, powers the control unit 138 and powers the electric motor 128 via a line 142.

The control unit 138 comprises a demodulator and a microprocessor. The demodulator demodulates digital signals sent from the external control unit 136. The microprocessor of the control unit 138 receives the digital packet, decodes it and, provided that the power supply of the energiser unit 126 has sufficient energy stored, sends a signal via a signal line 144 to the motor 128 to either contract or enlarge the restriction device depending on the received command code.

Alternatively, the energy stored in the energy storage device of the energiser unit may only be used for powering a switch, and the energy for powering the motor 128 may be obtained from another implanted energy source of relatively high capacity, for example a battery. In this case the switch is adapted to connect said battery to the control unit 138 in an on mode when said switch is powered by the energy storage device and to keep the battery disconnected from the control unit in a standby mode when the switch is not powered.

Figure 17:
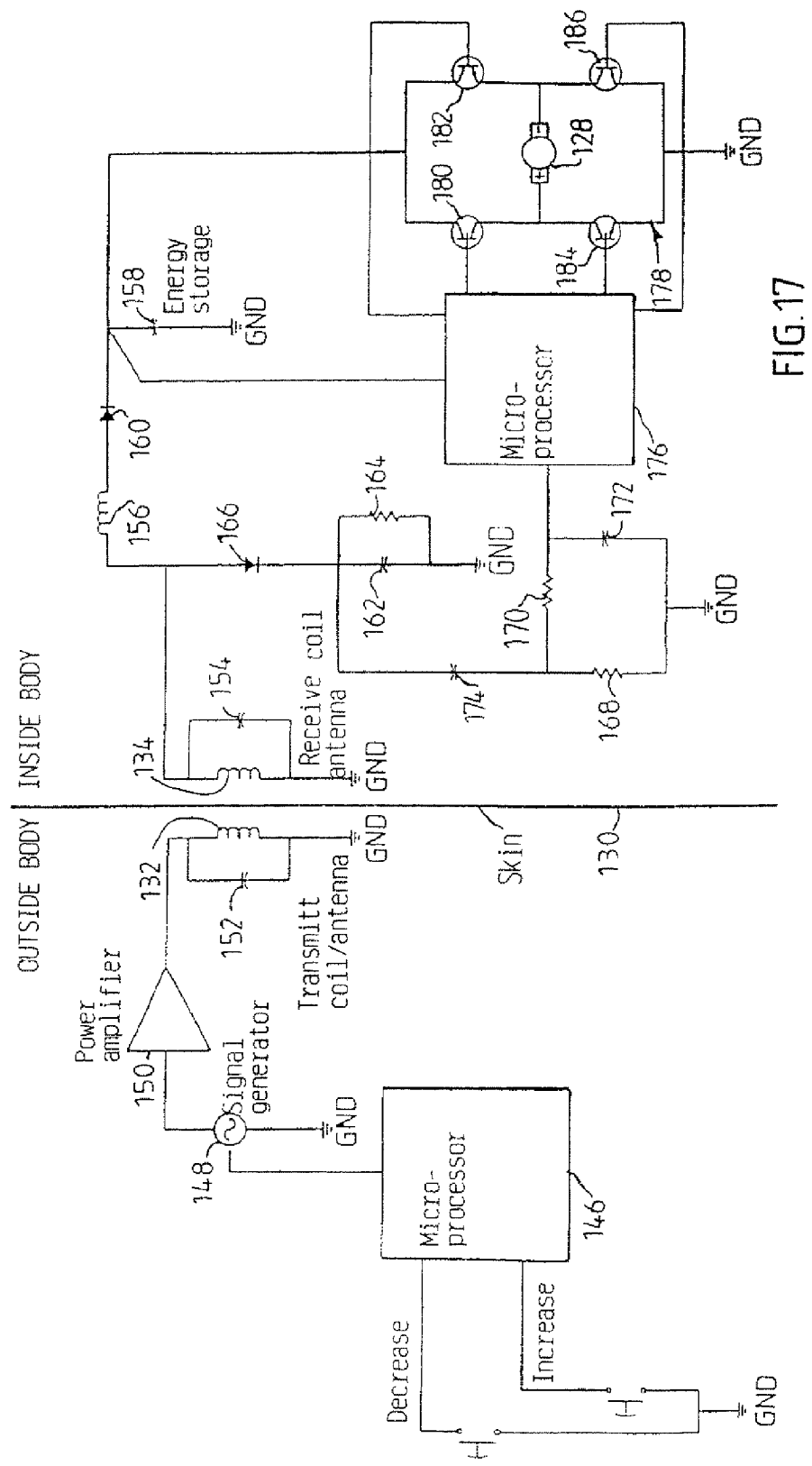
FIG. 17 is a schematic view of exemplary circuitry used for the components of the block diagram of FIG. 16.

With reference to FIG. 17, the remote control schematically described above will now be described in accordance with a more detailed embodiment. The external control unit 136 comprises a microprocessor 146, a signal generator 148 and a power amplifier 150 connected thereto. The microprocessor 146 is adapted to switch the signal generator 148 on/off and to modulate signals generated by the signal generator 148 with digital commands that are sent to implanted components of the apparatus. The power amplifier 150 amplifies the signals and sends them to the external signal transmitting antenna 132. The antenna 132 is connected in parallel with a capacitor 152 to form a resonant circuit tuned to the frequency generated by the signal generator 148.

The implanted signal receiving antenna coil 134 forms together with a capacitor 154 a resonant circuit that is tuned to the same frequency as the transmitting antenna 132. The signal receiving antenna coil 134 induces a current from the received high frequency electromagnetic waves and a rectifying diode 160 rectifies the induced current, which charges a storage capacitor 158. A coil 156 connected between the antenna coil 134 and the diode 160 prevents the capacitor 158 and the diode 160 from loading the circuit of the signal receiving antenna 134 at higher frequencies. Thus, the coil 156 makes it possible to charge the capacitor 158 and to transmit digital information using amplitude modulation.

A capacitor 162 and a resistor 164 connected in parallel and a diode 166 forms a detector used to detect amplitude modulated digital information. A filter circuit is formed by a resistor 168 connected in series with a resistor 170 connected in series with a capacitor 172 connected in series with the resistor 168 via ground, and a capacitor 174, one terminal of which is connected between the resistors 168,170 and the other terminal of which is connected between the diode 166 and the circuit formed by the capacitor 162 and resistor 164. The filter circuit is used to filter out undesired low and high frequencies. The detected and filtered signals are fed to an implanted microprocessor 176 that decodes the digital information and controls the motor 128 via an H-bridge 178 comprising transistors 180, 82,184 and 186. The motor 128 can be driven in two opposite directions by the H-bridge 178.

The microprocessor 176 also monitors the amount of stored energy in the storage capacitor 158. Before sending signals to activate the motor 128, the microprocessor 176 checks whether the energy stored in the storage capacitor 158 is enough. If the stored energy is not enough to perform the requested operation, the microprocessor 176 waits for the received signals to charge the storage capacitor 158 before activating the motor 128.

The invention claimed is:

1. A male sexual impotence treatment apparatus, comprising:
   an operable restriction device implantable in an impotent patient for engaging a tissue portion of the normal penile tissue or the prolongation thereof to form a restrictable penile exit blood flow passageway,
   an energy transmission device for wireless transmission of energy from outside the patient's body to inside the patient's body for use in connection with the operation of the restriction device, including temporarily contracting said tissue portion to restrict the penile exit blood flow in the blood flow passageway to achieve erection, wherein said energy transmission device transmits energy of a first form and the restriction device is operable in response to energy of a second form,
   a receiving coil antenna implantable in the patient for receiving the transmitted energy, the receiving coil antenna comprising a resonant circuit comprising a capacitor and a coil, which together form the resonant circuit, the resonant circuit and the energy transmission device being tuned to the same frequency,
   an energy transforming device implantable in the patient for transforming the energy of the first form wirelessly transmitted by the energy transmission device into the energy of the second form, the second form of energy being electric energy,
   the restriction device being powered with the second form of energy both during the temporary contraction of said penile tissue portion or the prolongation thereof to achieve erection and during the release of said restriction device to release the tissue portion for releasing the penile exit blood flow in the blood flow passageway to achieve flaccid state of the penis, the operation of the restriction device being reversed when the polarity of the second form of energy is reversed,
   a switch implantable in the patient for directly or indirectly switching the operation of the restriction device, and
   a source of energy implantable in the patient, the switch being operated by the energy of the second form supplied by the energy storage device to switch from an off mode, in which the source of energy is not in use, to an on mode, in which the source of energy supplies energy for the operation of the restriction device.

2. An apparatus according to claim 1, wherein the energy of the second form is different than the energy of the first form.

3. An apparatus according to claim 1, wherein the energy transforming device comprises at least one element having a positive region and a negative region, the element is capable of creating an energy field between the positive and negative regions when exposed to the energy of the first form transmitted by the energy transmission device, and the energy field produces the energy of the second form.

4. An apparatus according to claim 3, wherein the element comprises an electrical junction element, and the electrical junction element is capable of inducing an electric field between the positive and negative regions when exposed to the energy of the first form transmitted by the energy transmission device, whereby the energy of the second form comprises electric energy.

5. An apparatus according to claim 4, wherein the restriction device is electrically operated, and the positive and negative regions of the electrical junction element supply electric energy for the operation of the restriction device.

6. An apparatus according to claim 5, further comprising electric conductors connected to the positive and negative regions of the electrical junction element, whereby the electrical junction element is capable of supplying an electric current via the conductors.

7. An apparatus according to claim 6, wherein the electrical junction element is capable of supplying a direct current or pulsating direct current via the conductors.

8. An apparatus according to claim 6, wherein the electrical junction element is capable of supplying an alternating current or a combination of a direct and alternating current via the conductors.

9. An apparatus according to claim 5, wherein the electrical junction element is capable of supplying a frequency or amplitude modulated signal.

10. An apparatus according to claim 5, wherein the electrical junction element is capable of supplying an analog or digital signal.

11. An apparatus according to claim 1, wherein the energy transforming device forms a flat and thin sheet, and has a volume of less than 2000 cm$^3$.

12. An apparatus according to claim 1, wherein the energy transforming device is adapted to transform the energy of the first form directly or indirectly into the energy of the second form.

13. An apparatus according to claim 12, further comprising an implantable motor or pump for operating the restriction device, wherein the motor or pump is powered by the energy of the second form.

14. An apparatus according to claim 13, wherein the energy transforming device is adapted to directly power the motor or pump by the transformed energy, as the energy of the second form is being transformed from the energy of the first form.

15. An apparatus according to claim 12, wherein the wireless energy of the first form comprises sound waves and the energy of the second form comprises electric energy.

16. An apparatus according to claim 1, wherein the energy transforming device comprises a capacitor and the energy of the second form comprises electric energy.

17. An apparatus according to claim 16, wherein the capacitor is adapted to produce electric pulses from the transformed electric energy.

18. An apparatus according to claim 17, wherein the capacitor is adapted to produce the pulses of the electric energy, as the energy transforming device transforms the energy of the first form transmitted by the energy transmission device into the electric energy of the second form.

19. An apparatus according to claim 1, further comprising an implantable stabiliser for stabilising the energy of the second form.

20. An apparatus according to claim 19, wherein the energy of the second form comprises electric current and the stabiliser comprises at least one capacitor.

21. An apparatus according to claim 1, further comprising implantable electrical components including at least one voltage level guard.

22. An apparatus according to claim 1, further comprising implantable electrical components including a single voltage level guard.

23. An apparatus according to claim 21, wherein the electrical components are devoid of any current detector and/or charge level detector.

24. An apparatus according to claim 21, further comprising an implantable capacitor or accumulator, wherein the charge or discharge of the capacitor or accumulator is controlled by use of the voltage level guard.

25. An apparatus according to claim 16, wherein the capacitor has a capacity less than 0.1 µF.

26. An apparatus according to claim 1, wherein the energy transmission device is adapted to transmit wireless energy for direct use in connection with the operation of the restriction device, as the wireless energy is being transmitted.

27. An apparatus according to claim 26, further comprising an implantable motor or pump for operating the restriction device, wherein the energy transmission device is adapted to directly power the motor or pump with wireless energy.

28. An apparatus according to claim 27, wherein the energy transmission device is adapted to transmit wireless energy in the form of a magnetic field or electromagnetic waves for direct power of the motor or pump.

29. An apparatus according to claim 1, wherein the energy transforming device is adapted to supply the energy of the second form for direct use in connection with the operation of the restriction device, as the energy of the first form is being transformed into the energy of the second form.

30. An apparatus according to claim 29, further comprising an implantable motor or pump for operating the restriction device, wherein the energy transforming device is adapted to directly power the motor or pump with the energy of the second form.

31. An apparatus according to claim 30, wherein the energy transforming device directly operates the restriction device with the energy of the second form in a non-magnetic, non-thermal or non-mechanical manner.

32. An apparatus according to claim 1, further comprising an implantable motor for direct or intermittent operation of the restriction device, wherein the energy transforming device powers the motor with the energy of the second form.

33. An apparatus according to claim 32, wherein the restriction device is operable to perform a reversible function and the motor is capable of reversing said function.

34. An apparatus according to claim 1, wherein the restriction device comprises a hydraulic restriction device, and further comprising an implantable pump for operating the hydraulic restriction device, the energy transforming device supplying the energy of the second form for driving the pump.

35. An apparatus according to claim 27, wherein the pump is not a plunger type of pump.

36. An apparatus according to claim 1, wherein the energy transforming device is capable of generating as the energy of the second form a current exceeding 1 µA, when transferring the energy of the first form transmitted by the energy transmission device.

37. An apparatus according to claim 1, further comprising an adjustment device for adjusting the restriction device to change the restriction of the blood flow passageway, wherein the adjustment device is adapted to mechanically adjust the restriction device, or adapted to hydraulically adjust the restriction device by using hydraulic means which is devoid of hydraulic fluid of the kind having a viscosity that substantially increases when exposed to heat or a magnetic field.

38. An apparatus according to claim 1, wherein the energy transforming device comprises at least one semiconductor type of component.

39. An apparatus according to claim 38, wherein the energy transforming device comprises a circuitry of semiconductor components.

40. An apparatus according to claim 38, wherein the semiconductor component comprises a transistor or microchip or similar electronic components excluding rectifying diodes.

41. An apparatus according to claim 39, wherein the semiconductor component comprises at least one element having a positive region and a negative region, the element is capable of creating an energy field between the positive and negative regions when exposed to the energy of the first form transmitted by the energy transmission device, and the energy field produces the energy of the second form.

42. An apparatus according to claim 1, further comprising an implantable operation device for operating the restriction device and a control device for controlling the operation device.

43. An apparatus according to claim 42, wherein the operation device comprises a motor.

44. An apparatus according to claim 32, further comprising an implantable gearing connected to the motor.

45. An apparatus according to claim 42, wherein the motor comprises a rotary motor and the control device controls the rotary motor to rotate a desired number of revolutions.

46. An apparatus according to claim 43, wherein the motor comprises a linear motor.

47. An apparatus according to claim 42, wherein the motor comprises a hydraulic or pneumatic fluid motor, and the control device controls the fluid motor.

48. An apparatus according to claim 43, wherein the motor comprises an electric motor having electrically conductive parts made of plastics.

49. An apparatus according to claim 42, wherein the restriction device comprises hydraulic means and the operation device is adapted to conduct a hydraulic fluid in the hydraulic means.

50. An apparatus according to claim 49, wherein the operation device comprises a fluid conduit connected to the hydraulic means of the restriction device, and a reservoir for fluid, the reservoir forming part of the conduit.

51. An apparatus according to claim 50, wherein the hydraulic means and conduit are devoid of any non-return valve.

52. An apparatus according to claim 51, wherein the reservoir forms a fluid chamber with a variable volume, and the operation device is adapted to distribute fluid from the chamber to the hydraulic means of the restriction device by reduction of the volume of the chamber and to withdraw fluid from the hydraulic means to the chamber by expansion of the volume of the chamber.

53. An apparatus according to claim 52, wherein the operation device comprises an implantable motor used for reducing and expanding the volume of the chamber.

54. An apparatus according to claim 49, wherein the operation device comprises an implantable pump for pumping the hydraulic fluid in the hydraulic means of the restriction device.

55. An apparatus according to claim 42, wherein the control device shifts polarity of the energy of the second form to reverse the operation device.

56. An apparatus according to claim 43, wherein the operation device comprises an electric motor and the energy of the second form comprises electric energy.

57. An apparatus according to claim 1, further comprising a reversing device implantable in the patient for reversing the function performed by the restriction device.

58. An apparatus according to claim 42, wherein the control device controls the reversing device to reverse the function performed by the restriction device.

59. An apparatus according to claim 57, wherein the reversing device comprises hydraulic means including a valve for shifting the flow direction of a fluid flow in the hydraulic means.

60. An apparatus according to claim 57, wherein the reversing device comprises a mechanical reversing device.

61. An apparatus according to claim 60, wherein the reversing device comprises a gearbox.

62. An apparatus according to claim 57, wherein the reversing device comprises a switch.

63. An apparatus according to claim 62, wherein the switch is operable by the energy of the second form.

64. An apparatus according to claim 63, wherein the control device controls the operation of the switch by shifting polarity of the energy of the second form.

65. An apparatus according to claim 63, wherein the switch comprises an electric switch and the energy of the second form comprises electric energy.

66. An apparatus according to claim 42, wherein the operation device comprises hydraulic means and at least one valve for controlling a fluid flow in the hydraulic means.

67. An apparatus according to claim 66, further comprising a wireless remote control for controlling the valve.

68. An apparatus according to claim 17, wherein the control device is adapted to control the energy transforming device to produce the energy of the second form in a train of energy pulses for direct use in connection with the operation of the restriction device.

69. An apparatus according to claim 1, further comprising an energy storage device implantable in the patient for storing the energy of the second form and for supplying energy in connection with the operation of the restriction device.

70. An apparatus according to claim 69, wherein the energy storage device comprises an accumulator.

71. An apparatus according to claim 70, wherein the energy of the second form comprises electric energy and the energy storage device comprises an electric accumulator.

72. An apparatus according to claim 71, wherein the electric accumulator comprises at least one capacitor or at least one rechargeable battery, or a combination of at least one capacitor and at least one rechargeable battery.

73. An apparatus according to claim 1, further comprising a source of energy implantable in the patient, and a remote control for controlling the supply of energy of the source of energy, wherein the switch is operated by the energy of the second form supplied by the energy storage device to switch from an off mode, in which the remote control is prevented from controlling the source of energy and the source of energy is not in use for a standby mode, to a standby mode, in which the remote control is permitted to control the source of energy to supply energy for the operation of the restriction device.

74. An apparatus according to claim 1, further comprising a source of energy implantable in the patient for supplying energy for the operation of the restriction device, wherein the switch is operated by the energy of the second form supplied by the energy transforming device to switch from an off mode, in which the source of energy is not in use, to an on mode, in which the source of energy supplies energy for the operation of the restriction device.

75. An apparatus according to claim 1, further comprising a source of energy implantable in the patient for supplying energy for the operation of the restriction device, and a remote control for controlling the supply of energy of the implantable source of energy, wherein the switch is operated by the energy of the second form supplied by the energy transforming device to switch from an off mode, in which the remote control is prevented from controlling the source of energy and the source of energy is not in use for a standby mode, to a standby mode, in which the remote control is permitted to control the source of energy to supply energy for the operation of the restriction device.

76. An apparatus according to claim 1, further comprising a source of energy implantable in the patient for supplying energy for the operation of the restriction device, wherein the switch is operated by the energy of the first form supplied by the energy transmission device to switch from an off mode, in which the source of energy is not in use, to an on mode, in which the source of energy supplies energy for the operation of the restriction device.

77. An apparatus according to claim 1, further comprising a source of energy implantable in the patient for supplying energy for the operation of the restriction device, and a remote control for controlling the supply of energy of the implantable source of energy, wherein the switch is operated by the energy of the first form supplied by the energy transmission device to switch from an off mode, in which the remote control is prevented from controlling the source of energy and the source of energy is not in use, to a standby mode, in which the remote control is permitted to control the source of energy to supply energy for the operation of the restriction device.

78. An apparatus according to claim 1, wherein the restriction device is electrically operated, and the energy of the second form comprises electric energy.

79. An apparatus according to claim 78, further comprising electric conductors connected to the energy transforming device, whereby the energy transforming device is capable of supplying an electric current via the conductors.

80. An apparatus according to claim 1, wherein the energy transforming device is capable of supplying a frequency, amplitude or frequency and amplitude modulated signal.

81. An apparatus according to claim 1, wherein the energy transforming device is capable of supplying an analog, digital or a combination of an analog and digital signal.

82. An apparatus according to claim 1, further comprising an activatable source of energy implantable in the patient, wherein the source of energy is activated by wireless energy transmitted by the energy transmission device, to supply energy which is used in connection with the operation of the restriction device.

83. An apparatus according to claim 1, wherein the energy transmission device transmits energy by at least one wireless signal.

84. An apparatus according to claim 83, wherein the signal contains radiant energy.

85. An apparatus according to claim 83, wherein the signal comprises a wave signal.

86. An apparatus according to claim 85, wherein the wave signal comprises an electromagnetic wave signal including one of an infrared light signal, a visible light signal, an ultra violet light signal, a laser signal, a micro wave signal, a radio wave signal, an x-ray radiation signal, and a gamma radiation signal.

87. An apparatus according to claim 85, wherein the wave signal comprises a sound or ultrasound wave signal.

88. An apparatus according to claim 83, wherein the signal comprises a digital or analog signal, or a combination of a digital and analog signal.

89. An apparatus according to claim 1, wherein the energy of the first form transmitted by the energy transmission device comprises an electric, an electromagnetic or a magnetic field, or a combination thereof.

90. An apparatus according to claim 89, wherein the electric, electromagnetic or magnetic field, or the combination thereof is transmitted in pulses or digital pulses, or a combination of pulses and digital pulses by the energy transmission device.

91. An apparatus according to claim 1, wherein the energy of a first form transmitted by the energy transmission device comprises an electric, an electromagnetic or a magnetic field, or a combination thereof.

92. An apparatus according to claim 91, wherein the electric, electromagnetic or magnetic field, or the combination thereof is transmitted in waves or analog pulses or a combination thereof by the energy transmission device.

93. An apparatus according to claim 1, wherein the energy transmitted by the energy transmission device comprises polarised energy.

94. An apparatus according to claim 1, wherein the energy transforming device transforms the energy of the first form into a direct current or pulsating direct current, or a combination of a direct current and pulsating direct current.

95. An apparatus according to claim 1, wherein the energy transforming device transforms the energy of the first form into an alternating current or a combination of a direct and alternating current.

96. An apparatus according to claim 1, further comprising an implantable pulse generator for generating electrical pulses from the energy of the second form produced by the energy field.

97. An apparatus according to claim 1, further comprising at least one implantable sensor for sensing at least one physical parameter of the patient.

98. An apparatus according to claim 97, wherein the sensor comprises a pressure sensor for directly or indirectly sensing as the physical parameter the pressure in the blood flow passageway.

99. An apparatus according to claim 97, further comprising a control device for controlling the restriction device in response to signals from the sensor.

100. An apparatus according to claim 99, wherein the control device comprises an internal control unit implantable in the patient for controlling the restriction device in response to signals from the sensor.

101. An apparatus according to claim 100, wherein the internal control unit directly controls the restriction device in response to signals from the sensor.

102. An apparatus according to claim 99, wherein the control device comprises an external control unit outside the patient's body for controlling the restriction device in response to signals from the sensor.

103. An apparatus according to claim 102, wherein the external control unit stores information on the physical parameter sensed by the sensor and is manually operated to control the restriction device based on the stored information.

104. An apparatus according to claim 97, further comprising at least one implantable sender for sending information on the physical parameter sensed by the sensor.

105. An apparatus according to claim 1, further comprising a wireless remote control for transmitting at least one wireless remote control for controlling the restriction device.

106. An apparatus according to claim 105, wherein the control signal comprises a frequency, amplitude or frequency or amplitude modulated signal.

107. An apparatus according to claim 105, wherein the control signal comprises an analog or a digital signal, or a combination of an analog and digital signal.

108. An apparatus according to claim 105, wherein the remote control is capable of obtaining information on the condition of the implantable restriction device and to control the restriction device in response to the information.

109. An apparatus according to claim 105, wherein the remote control comprises an implantable control unit for controlling the restriction device.

110. An apparatus according to claim 109, wherein the control unit comprises a microprocessor.

111. An apparatus according to claim 105, wherein the wireless remote control comprises at least one external signal transmitter or transceiver and at least one internal signal receiver or transceiver implantable in the patient.

112. An apparatus according to claim 105, wherein the wireless remote control comprises at least one external signal receiver or transceiver and at least one internal signal transmitter or transceiver implantable in the patient.

113. An apparatus according to claim 105, wherein the remote control is capable of sending information related to the restriction device from inside the patient's body to the outside thereof.

114. An apparatus according to claim 113, wherein the remote control controls the restriction device in response to the information.

115. An apparatus according to claim 105, wherein the remote control comprises a control signal transmitter for transmitting the wireless control signal, and the energy transmission device comprises the control signal transmitter, whereby energy is transmitted by the control signal.

116. An apparatus according to claim 105, wherein the energy transmission device transmits energy by at least one signal separate from the control signal.

117. An apparatus according to claim 105, wherein the remote control transmits a carrier signal for carrying the control signal.

118. An apparatus according to claim 105, wherein the energy transmission device transmits energy by at least one signal, which is used as a carrier signal for the control signal transmitted by the remote control.

119. An apparatus according to claim 118, wherein the carrier signal is frequency, amplitude or frequency and amplitude modulated.

120. An apparatus according to claim 118, wherein the carrier signal comprises digital, analog or a combination of digital and analog signals.

121. An apparatus according to claim 120, wherein the signals comprise wave signals.

122. An apparatus according to claim 105, wherein the control signal comprises a wave signal comprising one of a sound wave signal, an ultrasound wave signal, an electromagnetic wave signal, an infrared light signal, a visible light signal, an ultra violet light signal, a laser light signal, a micro wave signal, a radio wave signal, an x-ray radiation signal and a gamma radiation signal.

123. An apparatus according to claim 105, wherein the control signal comprises an electric or magnetic field, or a combined electric and magnetic field.

124. An apparatus according to claim 107, wherein the remote control transmits an electromagnetic carrier wave signal for carrying the digital or analog control signal.

125. An apparatus according to claim 1, wherein the energy of the second form used for operating the restriction device is wirelessly transmitted by the energy transforming device.

126. An apparatus according to claim 1, further comprising an implantable control unit for controlling the restriction device.

127. An apparatus according to claim 126, wherein the control unit is programmable for controlling the restriction device in accordance with a program.

128. An apparatus according to claim 126, wherein the control unit controls the restriction device over time in accordance with an activity schedule program.

129. An apparatus according to claim 126, further comprising an external wireless remote control for programming the implantable control unit.

130. An apparatus according to claim 1, further comprising an external data communicator and an implantable internal data communicator communicating with the external data communicator, wherein the internal communicator feeds data related to the restriction device back to the external data communicator or the external data communicator feeds data to the internal data communicator.

131. An apparatus according to claim 130, wherein the internal data communicator feeds data related to at least one physical signal of the patient.

132. An apparatus according to claim 1, wherein the restriction device is adapted to control the restriction of the blood flow passageway when implanted.

133. An apparatus according to claim 1, wherein the restriction device is non-inflatable.

134. An apparatus according to claim 1, wherein one of the energy of the first form and the energy of the second form comprises magnetic energy, kinetic energy, sound energy, chemical energy, radiant energy, electromagnetic energy, photo energy, nuclear energy or thermal energy.

135. An apparatus according to claim 1, wherein one of the energy of the first form and the energy of the second form is non-magnetic, non-kinetic, non-chemical, non-sonic, non-nuclear or non-thermal.

136. An apparatus according to claim 1, wherein the energy transforming device is designed to be implanted subcutaneously or in the abdomen, thorax or cephalic region of the patient.

137. An apparatus according to claim 1, wherein the energy transforming device is designed to be implanted in an orifice of the patient's body and under the mucosa or intraluminar outside the mucosa of the orifice.

138. An apparatus according to claim 1, wherein the energy transforming means is designed to be implanted in the retropritoneum or in the scrotum of the patient.

139. An apparatus according to claim 1, wherein the restriction device is embedded in a soft or gel-like material.

140. An apparatus according to claim 1, wherein the restriction device is embedded in a silicone material having hardness less than 20 Shore.

141. An apparatus according to claim 97, wherein the sensor is adapted to sense ejaculation as the physical parameter, and the restriction device is adapted to release the penile tissue or the prolongation thereof in response to the sensor sensing ejaculation.

142. An apparatus according to claim 1, further comprising a source of energy implantable in the patient, and a remote control for controlling the supply of energy of the source of energy, wherein the switch is operated by at least one of:

the energy of the second form supplied by the energy storage device to switch from an off mode, in which the remote control is prevented from controlling the source of energy and the source of energy is not in use for a standby mode, to a standby mode, in which the remote control is permitted to control the source of energy to supply energy for the operation of the restriction device, or the energy of the second form supplied by the energy transforming device to switch from an off mode, in which the remote control is prevented from controlling the source of energy and the source of energy is not in use for a standby mode, to a standby mode, in which the remote control is permitted to control the source of energy to supply energy for the operation of the restriction device.

\* \* \* \* \*